United States Patent
Hu et al.

(10) Patent No.: US 10,244,990 B2
(45) Date of Patent: Apr. 2, 2019

(54) SYSTEMS AND METHODS FOR REHABILITATION OF LIMB MOTION

(71) Applicant: Board of Trustees of The University of Alabama, Tuscaloosa, AL (US)

(72) Inventors: Fei Hu, Tuscaloosa, AL (US); Rui Ma, Tuscaloosa, AL (US)

(73) Assignee: THE BOARD OF TRUSTEES OF THE UNIVERSITY OF ALABAMA, Tuscaloosa, AL (US)

( * ) Notice: Subject to any disclaimer, the term of this patent is extended or adjusted under 35 U.S.C. 154(b) by 144 days.

(21) Appl. No.: 15/281,526

(22) Filed: Sep. 30, 2016

(65) Prior Publication Data
US 2017/0087416 A1    Mar. 30, 2017

Related U.S. Application Data

(60) Provisional application No. 62/235,019, filed on Sep. 30, 2015.

(51) Int. Cl.
*A61B 5/00* (2006.01)
*A61B 5/11* (2006.01)
(Continued)

(52) U.S. Cl.
CPC ............ *A61B 5/7282* (2013.01); *A61B 5/112* (2013.01); *A61B 5/4023* (2013.01); *A61B 5/6829* (2013.01); *A61B 5/7257* (2013.01); *G06F 19/00* (2013.01); *G06K 9/00348* (2013.01); *G06K 9/00543* (2013.01); *G06K 9/469* (2013.01);
(Continued)

(58) Field of Classification Search
None
See application file for complete search history.

(56) References Cited

U.S. PATENT DOCUMENTS 8,852,129 B2 * 10/2014 Lee ...................... A61B 5/1101
600/595
8,915,132 B1 * 12/2014 Ward ...................... A61B 5/103
73/172
(Continued)

FOREIGN PATENT DOCUMENTS

WO    2012/176200    12/2012
WO    2012176200     12/2012

OTHER PUBLICATIONS

Pappas, et al., "A reliable, gyroscope based gait phase detection sensor embedded in a shoe insole," IEEE Sensors Journal, Apr. 2004.
(Continued)

*Primary Examiner* — Sundhara M Ganesan
(74) *Attorney, Agent, or Firm* — Meunier Carlin & Curfman LLC

(57) ABSTRACT

Systems and methods for rehabilitation of limb motion are described herein. An example system can include a thermal imaging device for imaging a subject or a plurality of sensors for sensing force or pressure exerted by a portion of the subject's body. The system can also include a processor and a memory operably coupled to the processor. The processor can be configured to receive force or pressure data measured by the sensors or image data captured by the thermal imaging device, and calculate a quantitative measure of the subject's limb motion based on the force or pressure data or the image data.

18 Claims, 22 Drawing Sheets

(51) Int. Cl.
| | |
|---|---|
| G06F 19/00 | (2018.01) |
| G06K 9/00 | (2006.01) |
| G06K 9/46 | (2006.01) |
| G06T 7/12 | (2017.01) |
| G06T 7/194 | (2017.01) |
| G16H 30/20 | (2018.01) |
| G16H 20/30 | (2018.01) |
| A63B 69/00 | (2006.01) |
| A63B 71/00 | (2006.01) |
| A63B 71/06 | (2006.01) |
| A63B 22/02 | (2006.01) |

(52) U.S. Cl.
CPC ............... *G06T 7/12* (2017.01); *G06T 7/194* (2017.01); *G16H 20/30* (2018.01); *G16H 30/20* (2018.01); *A61B 2505/09* (2013.01); *A61B 2562/0219* (2013.01); *A61B 2562/0247* (2013.01); *A63B 22/02* (2013.01); *A63B 69/0064* (2013.01); *A63B 71/0009* (2013.01); *A63B 71/0622* (2013.01); *A63B 2071/065* (2013.01); *A63B 2071/0625* (2013.01); *A63B 2071/0655* (2013.01); *A63B 2220/17* (2013.01); *A63B 2220/51* (2013.01); *A63B 2220/56* (2013.01); *A63B 2220/803* (2013.01); *A63B 2220/806* (2013.01); *A63B 2225/50* (2013.01); *A63B 2230/50* (2013.01); *G06T 2207/10048* (2013.01); *G06T 2207/20044* (2013.01); *G06T 2207/30196* (2013.01)

(56) References Cited

U.S. PATENT DOCUMENTS

| | | | |
|---|---|---|---|
| 9,877,682 B2 * | 1/2018 | Craelius | ............... A61B 5/1107 |
| 2008/0167580 A1 | 7/2008 | Avni et al. | |
| 2009/0270768 A1 | 10/2009 | Lee | |
| 2012/0130280 A1 | 5/2012 | Lee | |

OTHER PUBLICATIONS

Hsu, et al., "Gait and Balance Analysis for Patients with Alzheimer's Disease Using an Inertial-Sensor-Based Wearable Instrument," IEEE Journal of Biomedical and Health Informatics, vol. 18, No. 6, pp. 1822-1830, Nov. 2014.

Hundza, et al., "Accurate and Reliable Gait Cycle Detection in Parkinson's Disease," IEEE Trans. Neural Syst. Rehabil. Eng., vol. 22, No. 1, pp. 127-137, Jan. 2014.

Lee, et al., "A Smartphone-Centric System for the Range of Motion Assessment in Stroke Patients," IEEE Journal of Biomedical and Health Informatics, vol. 18, No. 6, pp. 1839-1847, Nov. 2014.

Howell, et al., "Kinetic Gait Analysis Using a Low-Cost Insole," IEEE Trans. Bio. Eng., Mar. 2013.

Ayase, et al., "A method for supporting at-home fitness exercise guidance and at-home nursing care for the elders, video-based simple measurement system," 10th IEEE Intl. Conf. on e-Health Networking, Applications and Service (Healthcom 2008), pp. 182-186, Jul. 2008.

Ar et al., "A Computerized Recognition System for the Home-Based Physiotherapy Exercises Using an RGBD Camera," IEEE Trans. Neural Syst. Rehabil. Eng., vol. 22, No. 6, pp. 1160-1171, Nov. 2014.

Metcalf, et al., "Markerless Motion Capture and Measurement of Hand Kinematics: Validation and Application to Home-Based Upper Limb Rehabilitation," IEEE Trans. Bio. Eng., vol. 60, No. 8, pp. 2184-2192, Aug. 2013.

Das, et al., "Quantitative measurement of motor symptoms in Parkinson's disease: A study with full-body motion capture data," 2011 Annual International Conference of the IEEE Engineering in Medicine and Biology Society (EMBC), Aug. 2011.

Jaffe, et al., "Stepping over obstacles to improve walking in individuals with poststroke hemiplegia," Journal of Rehabilitation Research & Development, vol. 41, No. 3A, pp. 283-292, May-Jun. 2004.

Agostini, et al., "Segmentation and Classification of Gait Cycles," IEEE Trans. Neural Syst. Rehabil. Eng , vol. 22, No. 5, Sep. 2014.

Lin, et al., "Online Segmentation of Human Motion for Automated Rehabilitation Exercise Analysis," IEEE Trans. Neural Syst. Rehabil. Eng., May 2013.

Frank, et al., "Time Series Analysis Using Geometric Template Matching," IEEE Tran. Pattern Analysis and Machine Intelligence, vol. 35, No. 3, pp. 740-754, Mar. 2013.

Keogh, et al., "Derivative dynamic time warping," SIAM Int. Conf. on Data Mining (SDM), 2001.

Shimodaira, et al., "Dynamic Time-Alignment Kernel in Support Vector Machine," Proc. Neural Information Processing Systems, 2001.

Zhou, et al., "Hierarchical Aligned Cluster Analysis for Temporal Clustering of Human Motion," IEEE Tran. Pattern Analysis and Machine Intelligence, vol. 35, 2013.

Gong, et al., "Structured Time Series Analysis for Human Action Segmentation and Recognition," IEEE Tran. Pattern Analysis and Machine Intelligence, vol. 36, No. 7, pp. 1414-1427, Jul. 2014.

Liu, et al., "Finding periodicity in space and time," Sixth International Conference on Computer Vision, pp. 376-383, Jan. 1998.

Academy of Neurologic Physical Therapy, Professional Resources, available at http://www.neuropt.org/professional-resources/neurology-section-outcome-measures-recommendations/stroke (accessed Mar. 26, 2018).

Takens, "Detecting strange attractors in turbulence," Dynamical Systems and Turbulence, Warwick 1980, vol. 898, No. 3, pp. 366-381, 1981.

* cited by examiner

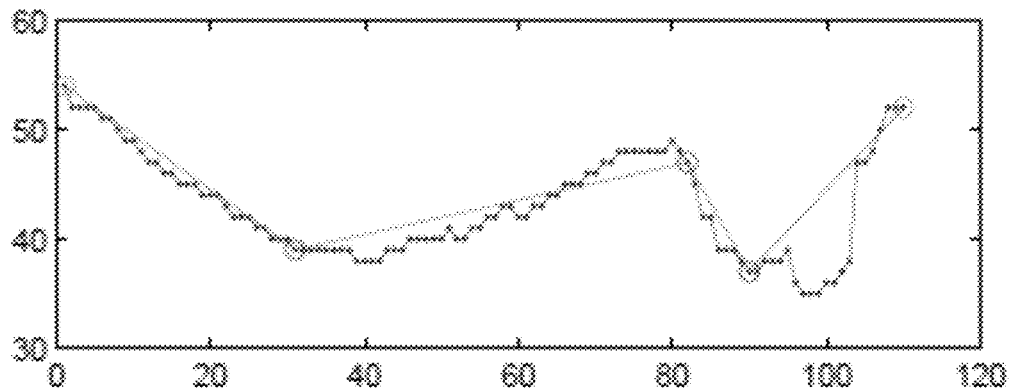
FIG. 4
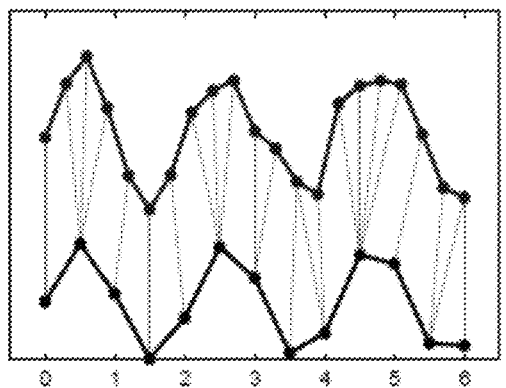 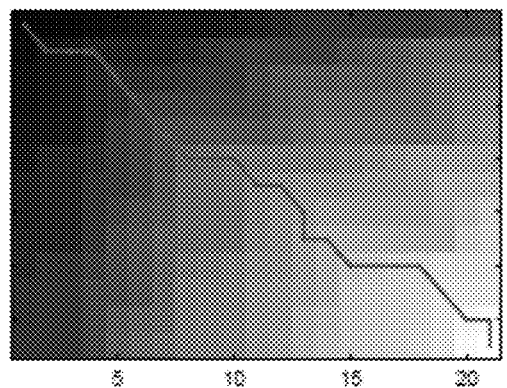
FIG. 5A           FIG. 5B input: $s_i, s_j$
output: *seg_point*

1. *peak_pattern_i* = find peaks in series $s_i$
2. *peak_pattern_j* = find peaks in series $s_j$
3. for all the part in *peak_pattern_i* do
4.    if *peak_pattern_i* = *peak_pattern_j* (part_k) do
5.      *seg_start_0* = *peak_position_j* [k]
6.      *seg_end_0* = *peak_position_j* [k+t]
7.      for *seg_start* = *seg_start_0* to *peak_position_j* [k-1] do
8.        compute *dist* ($s_i, s_j$ (*seg_start, seg_end_0*))
9.      end for
10.      if minimal *dist* < threshold do
11.        *seg_start_f* = the *seg_start* with minimal *dist*
12.      else *seg_start_f* = *peak_position_j* [k-1]
13.      for *seg_end* = *seg_end_0* to *peak_position_j* [k+t+1] do
14.        compute *dist* ($s_i, s_j$ (*seg_start_f, seg_end*))
15.      end for
16.      if minimal *dist* < threshold do
17.        *seg_end_f* = the *seg_end* with minimal *dist*
18.      else *seg_end_f* = *peak_position_j* [k+t+1]
19.      *seg_point* (iseg) = [*seg_start_f, seg_end_f*];
20. end for

*FIG. 12*

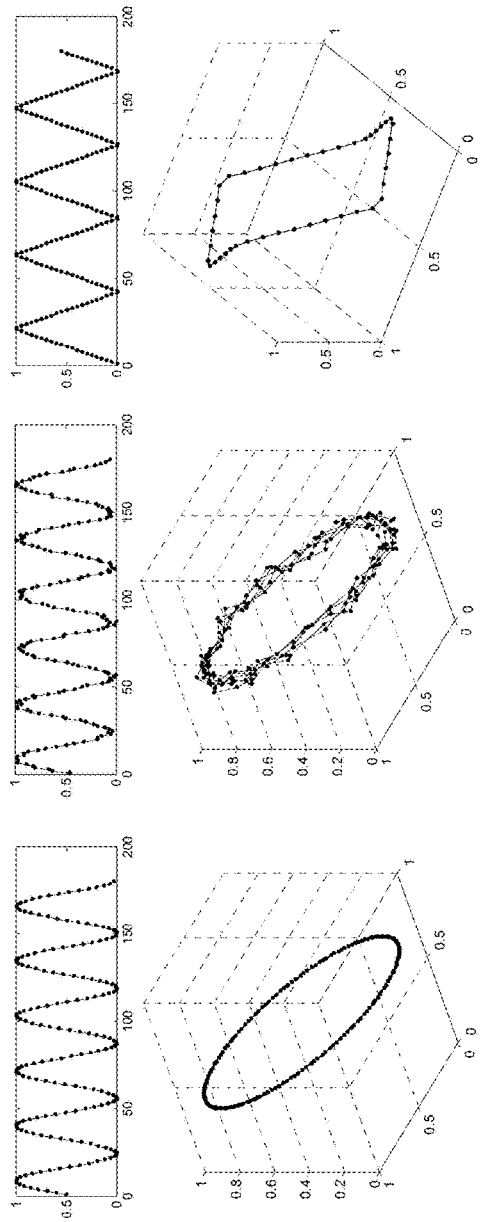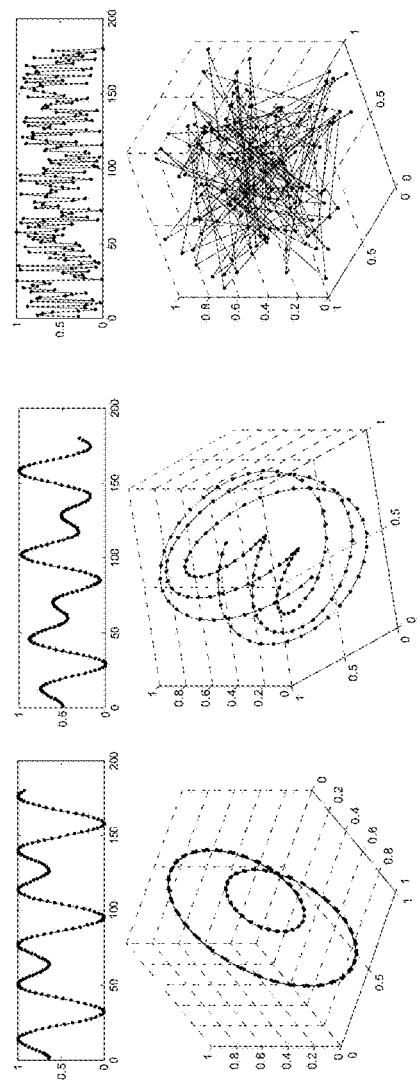

|  | Normal 1 | Normal 2 | Normal 3 | On toe | On outer edge | Right leg disabled | Left leg disabled |
|---|---|---|---|---|---|---|---|
| Normal 1 | 0.98 | 0.13 | 0.35 | 0 | 0 | 0 | 0 |
| Normal 2 | 0.23 | 0.88 | 0 | 0 | 0 | 0 | 0.25 |
| Normal 3 | 0.28 | 0.03 | 0.88 | 0 | 0 | 0.01 | 0.08 |
| On toe | 0 | 0 | 0 | 0.95 | 0 | 0 | 0 |
| On outer edge | 0 | 0 | 0 | 0 | 0.9 | 0 | 0 |
| Right leg disabled | 0 | 0 | 0.03 | 0 | 0 | 0.83 | 0 |
| Left leg disabled | 0.03 | 0.35 | 0.18 | 0 | 0 | 0 | 0.88 |

*FIG. 26*

SYSTEMS AND METHODS FOR REHABILITATION OF LIMB MOTION

CROSS-REFERENCE TO RELATED APPLICATIONS

This application claims the benefit of U.S. Provisional Patent Application No. 62/235,019, filed on Sep. 30, 2015, entitled "SYSTEMS AND METHODS FOR REHABILITATION OF LIMB MOTION," the disclosure of which is expressly incorporated herein by reference in its entirety.

STATEMENT REGARDING FEDERALLY FUNDED RESEARCH

This invention was made with government support under Grant nos. NSF CNS-1335263, NSF CNS-1059212, and NSF IIS-0915862 awarded by the U.S. National Science Foundation. The government has certain rights in the invention.

BACKGROUND

Recovery from a stroke or a spinal cord injury can be difficult and can sometimes be a life-long process. Many patients (also referred to herein as "subjects" or "humans") can improve their motion functions after receiving carefully directed physical training. In the rehabilitation programs, patients may be trained to sit, stand, and walk. The training can substantially help the patients regain their strength and endurance. Typically, patients go to hospitals or other medical facilities for rehabilitation, where medical professionals (e.g., nurses and/or therapists) guide the patients. The medical professionals are needed to observe the progress and correct the patients' gestures. Thus, rehabilitation costs can be very expensive. For example, the cost of physical therapy for stroke patients in the United States is about $28 billion per year (see e.g., Stroke Statistics, available at http://www.uhnj.org/stroke/stats.htm), and this number keeps going up since more and more people are having strokes today due to work stress, eating styles, and environmental factors.

Intelligent rehabilitation systems that reduce the cost of treatment have been proposed. These intelligent rehabilitation systems deploy known sensing systems, as well as machine learning techniques. Examples of sensing systems deployed in these intelligent rehabilitation systems include wearable, inertial sensors (I. P. I. Pappas, T. Keller, S. Mangold, M. R. Popovic, V. Dietz, M. Morari, "A reliable gyroscope-based gait-phase detection sensor embedded in a shoe insole," IEEE Sensors Journal, vol. 4, no. 2, pp. 268-274, April 2004; Y. L. Hsu, P. C. Chung, W. H. Wang, M. C. Pai, C. Y. Wang, C. W. Lin, H. L. Wu, J. S. Wang, "Gait and Balance Analysis for Patients With Alzheimer's Disease Using an Inertial-Sensor-Based Wearable Instrument," IEEE Journal of Biomedical and Health Informatics, vol. 18, no. 6, pp. 1822-1830, November 2014; S. R. Hundza, W. R. Hook, C. R. Harris, S. V. Mahajan, P. A. Leslie, C. A. Spani, L. G. Spalteholz, B. J. Birch, D. T. Commandeur, N. J. Livingston, "Accurate and Reliable Gait Cycle Detection in Parkinson's Disease," IEEE Trans. Neural Syst. Rehabil. Eng., vol. 22, no. 1, pp. 127-137, Jan. 2014; W. Lee, S. Yen, A. Tay, Z. Zhao, T. M. Xu, K. K. M. Ling, Y. Ng, E. Chew, A. L. K. Cheong, and G. K. C. Huat, "A Smartphone-Centric System for the Range of Motion Assessment in Stroke Patients," IEEE Journal of Biomedical and Health Informatics, vol. 18, no. 6, pp. 1839-1847, November 2014), video cameras (R. Ayase, T. Higashi, S. Takayama, S. Sagawa, and N. Ashida, "A method for supporting at-home fitness exercise guidance and at-home nursing care for the elders, video-based simple measurement system," 10th IEEE Intl. Conf. on e-Health Networking, Applications and Service (HEALTHCOM 2008), pp. 182-186, July 2008), MICROSOFT KINECT of MICROSOFT CORP. of REDMOND, Wash. (I. Ar and Y. S. Akgul, "A Computerized Recognition System for the Home-Based Physiotherapy Exercises Using an RGBD Camera," IEEE Trans. Neural Syst. Rehabil. Eng., vol. 22, no. 6, pp. 1160-1171, November 2014; C. D. Metcalf, R. Robinson, A. J. Malpass, T. P. Bogle, T. A. Dell, C. Harris and S. H. Demain, "Markerless Motion Capture and Measurement of Hand Kinematics: Validation and Application to Home-Based Upper Limb Rehabilitation," IEEE Trans. Bio. Eng., vol. 60, no. 8, pp. 2184-2192, August 2013), and marker-based systems for detecting markers on human body joints (S. Das, L. Trutoiu, A. Murai, D. Alcindor, M. Oh, F. D. Torre, and J. Hodgins, "Quantitative measurement of motor symptoms in Parkinson's disease: A study with full-body motion capture data," 2011 Annual International Conference of the IEEE Engineering in Medicine and Biology Society (EMBC), pp. 6789-6792, August 2011).

Unlike other applications such as smart homes, which only require coarse recognition of the human motions, a sensing system for intelligent rehabilitation training applications must recognize the motion of specific limbs or body parts with finer resolution. Conventional intelligent rehabilitation system have some limitations. For example, wearable, inertial sensors (e.g., accelerometers, gyroscopes, magnetometers, etc.) can be deployed on the joints of the human body to capture the motion of limbs. Although inertial sensors are good at detecting dynamic motion signals, inertial sensors are incapable of capturing real human postures since inertial sensors do not capture images of the subject's body. Inertial sensors are also susceptible to accumulating displacement errors. Video cameras and depth sensors (such MICROSOFT KINECT) can capture images, and skeleton patterns can be extracted for later posture recognition. However, video/depth image processing is computationally expensive, particularly when extracting motion patterns. In addition, video cameras and depth sensors are limited by the illumination conditions, obstacles, and limited field of view. Although it may be possible to apply processing techniques to overcome some of these limitations, such processing techniques increase computation costs even more. Marker-based sensing systems can accurately detect human posture, but due to high costs, deployment in intelligent rehabilitation system applications is not feasible.

SUMMARY

An example system for rehabilitation of limb motion is described herein. The system can include a thermal imaging device for imaging a subject or a plurality of sensors for sensing force or pressure exerted by a portion of the subject's body. The system can also include a processor and a memory operably coupled to the processor. The processor can be configured to receive force or pressure data measured by the sensors or image data captured by the thermal imaging device, and calculate a quantitative measure of the subject's limb motion based on the force or pressure data or the image data. In some implementations, the system optionally includes both the sensors and the thermal imaging device.

Additionally and optionally, the sensors can be configured to measure a respective pressure exerted by each of the subject's feet. Optionally, the sensors can be thin-film pressure sensors configured for placement in the subject's footwear. Alternatively or additionally, the sensors can optionally be configured to transmit the force or pressure data over a wireless link.

Alternatively or additionally, the thermal imaging device can optionally capture motion of the subject's lower limbs. Optionally, the thermal imaging device can be configured to transmit the image data over a wireless link.

Alternatively or additionally, the quantitative measure of the subject's limb motion can optionally be a height of raising a limb, a motion cycle similarity score, a quality of periodicity of limb trajectory, or a balance capability of the subject.

Alternatively or additionally, the system can optionally include a display device. Additionally and optionally, the processor can be further configured to generate an instruction related to the subject's limb motion based on the quantitative measure, and the instruction can be graphically displayed on the display device. For example, the instruction can optionally be a recommended change in: a height of limb motion, a direction of limb motion, a speed of limb motion, or a placement of the subject's foot.

In some implementations, the processor can optionally be further configured to extract a motion series from the image data, where the motion series defines the subject's limb motion in at least one dimension. Additionally, the processor can be further configured to recognize normal motion cycles within the motion series based on a comparison between a peak pattern of the motion series and a peak pattern of a template motion series (e.g., a series that defines a normal motion cycle). The peak pattern can include an amplitude, order, or speed of peaks. Additionally and optionally, the processor can be further configured to recognize abnormal motion cycles within the motion series based on a comparison between a peak pattern of the motion series and a peak pattern of a template motion series. Additionally and optionally, the quantitative measure of the subject's limb motion can be calculated as a motion cycle similarity score between one or more peaks within the motion series and one or more peaks within the template motion series. Optionally, a normal motion cycle can be recognized based on the motion cycle similarity score.

In some implementations, the quantitative measure of the subject's limb motion can optionally be calculated as a quality of periodicity of limb trajectory. For example, the processor can optionally be further configured to extract a motion series from the image data, where the motion series defines the subject's limb motion in at least one dimension. Additionally, the processor can optionally be configured to transform the motion series into a spatial domain. For example, the motion series can be transformed into a spatial domain using Time-Delay Embedding (TDE). The quantitative measure of the subject's limb motion can be calculated by deriving a quality of periodicity of limb trajectory based on the motion series in the spatial domain. For example, the quality of periodicity of limb trajectory can be derived by calculating a linear density of a shortest path of an attractor formed by the motion series in the spatial domain. Optionally, the subject's limb motion can optionally be a trajectory of at least a portion of the subject's foot. For example, the subject's limb motion can optionally be a trajectory of the subject's toe, the subject's heel, or the subject's foot angle.

In some implementations, the quantitative measure of the subject's limb motion can optionally be calculated as a balance capability. For example, the processor can optionally be further configured to determine a pressure distribution between the subject's feet. The quantitative measure of the subject's limb motion can be calculated by determining a balance capability of the subject based on the pressure distribution between the subject's feet. Optionally, the pressure distribution between the subject's feet can be a plantar pressure distribution.

Alternatively or additionally, the processor can optionally be further configured to identify a weak or disabled limb, an abnormal walking condition, or an imbalance of the subject.

An example method for rehabilitation of limb motion is described herein. The method can include receiving image data captured by a thermal imaging device for imaging a subject or force or pressure data measured by a plurality of sensors for sensing force or pressure exerted by a portion of the subject's body, and calculating a quantitative measure of the subject's limb motion based on the force or pressure data or the image data.

Additionally and optionally, the method can further include providing a recommendation for rehabilitation based on the quantitative measure of the subject's limb motion.

Alternatively or additionally, the sensors can optionally measure a respective pressure exerted by each of the subject's feet. Optionally, the force or pressure data can be received over a wireless link.

Alternatively or additionally, the thermal imaging device can capture motion of the subject's lower limbs. Optionally, the image data can be received over a wireless link.

Optionally, the quantitative measure of the subject's limb motion can be a height of raising a limb, a motion cycle similarity score, a quality of periodicity of limb trajectory, or a balance capability of the subject.

Alternatively or additionally, the method can optionally further include generating an instruction related to the subject's limb motion based on the quantitative measure, and transmitting the instruction for graphical display on a display device. For example, the instruction can be a recommended change in: a height of limb motion, a direction of limb motion, a speed of limb motion, or a placement of the subject's foot.

In some implementations, the method can optionally further include extracting a motion series from the image data, and recognizing a normal motion cycle within the motion series based on a comparison between a peak pattern of the motion series and a peak pattern of a template motion series (e.g., a series that defines a normal motion cycle). The motion series can optionally define the subject's limb motion in at least one dimension. The peak pattern can include an amplitude, order, or speed of peaks. Additionally and optionally, the method can further include recognizing an abnormal motion cycle within the motion series based on a comparison between a peak pattern of the motion series and a peak pattern of a template motion series. Additionally and optionally, the quantitative measure of the subject's limb motion can be calculated as a motion cycle similarity score between one or more peaks within the motion series and one or more peaks within the template motion series. Optionally, a normal motion cycle can be recognized based on the motion cycle similarity score.

In some implementations, the quantitative measure of the subject's limb motion can optionally be calculated as a quality of periodicity of limb trajectory. For example, the method can optionally further include extracting a motion series from the image data, and transforming the motion series into a spatial domain. The motion series can define the subject's limb motion in at least one dimension. In addition, the motion series can be transformed into a spatial domain using Time-Delay Embedding (TDE). The quantitative measure of the subject's limb motion can be calculated by deriving a quality of periodicity of limb trajectory based on the motion series in the spatial domain. For example, the quality of periodicity of limb trajectory can be derived by calculating a linear density of a shortest path of an attractor formed by the motion series in the spatial domain. Optionally, the subject's limb motion can optionally be a trajectory of at least a portion of the subject's foot. For example, the subject's limb motion can optionally be a trajectory of the subject's toe, the subject's heel, or the subject's foot angle.

In some implementations, the quantitative measure of the subject's limb motion can optionally be calculated as a balance capability. For example, the method can optionally further include determining a pressure distribution between the subject's feet. The quantitative measure of the subject's limb motion can be calculated by determining a balance capability of the subject based on the pressure distribution between the subject's feet. Optionally, the pressure distribution between the subject's feet can be a plantar pressure distribution.

Alternatively or additionally, the method can optionally further include identifying a weak or disabled limb, an abnormal walking condition, or an imbalance of the subject.

An example method of segmenting a time series is described herein. The method can include receiving a signal, identifying one or more peaks within the signal, matching a peak pattern of the signal to a peak pattern of a template signal, and calculating a similarity score between one or more peaks within the signal and one or more peaks within the template signal. A portion of the signal can be segmented based the similarity score. Optionally, the peak pattern can be an amplitude, order, or speed of peaks.

An example method of calculating a quantitative measure of periodicity of a signal is described herein. The method can include receiving a signal, transforming the signal into a spatial domain, identifying an attractor formed by the signal in the spatial domain, and calculating a quantitative measure of the periodicity of the signal based on the attractor. Optionally, the signal can be transformed into a spatial domain using Time-Delay Embedding (TDE). Additionally and optionally, the method can further include determining a linear length between at least two points of the attractor. Additionally, the method can optionally further include identifying a shortest linear length between at least two points of the attractor. The quantitative measure of the periodicity of the signal can be calculated as a linear density of a shortest linear length between at least two points of the attractor.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 4 is a graph illustrating the segmented linear regression of the edge of the subject's leg.

FIGS. 5A and 5B illustrate an example of DTW alignment (FIG. 5A) and the warping path of DTW in the cumulative similarity matrix (FIG. 5B).

FIG. 12 is the algorithm that implements the segmentation based on PMTW given in pseudo codes.

FIGS. 14A-14F illustrate the TDE reconstruction of some common 1-D time series (i.e., sinusoid, sinusoid with noise, sawtooth, synthetic sinusoid, complicated synthetic sinusoid, and random signal, respectively) in 3-D space.

FIG. 26 illustrates the confusion matrix of the classification of foot balance.

DETAILED DESCRIPTION

Figure 1A:
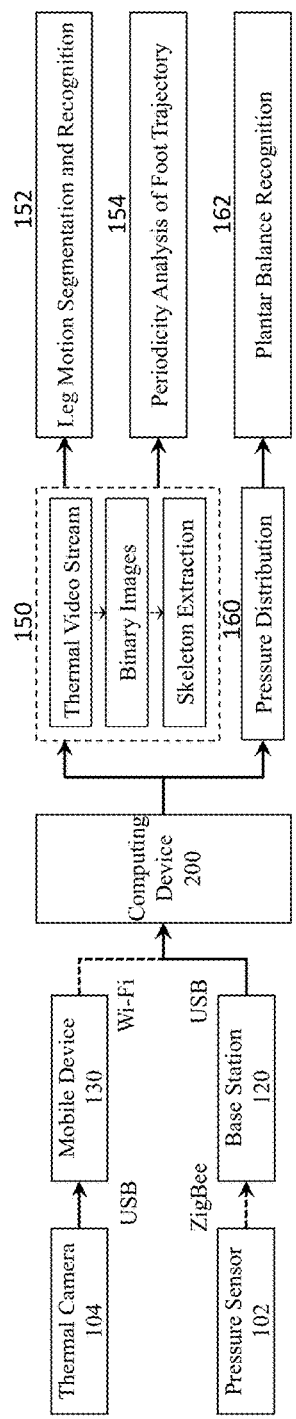
FIG. 1A is a block diagram of an example rehabilitation system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for rehabilitation of a subject's lower limb motion, it will become evident to those skilled in the art that the implementations are not limited thereto, but are applicable for rehabilitation of motion of other body parts including but not limited to upper limb motion rehabilitation. Additionally, while examples are provided herein for providing therapy to a subject who has suffered a stroke, it should be understood that the therapy can be provided to a subject who suffered other disabilities.

Described herein is an intelligent, low-cost system (also referred to herein as a "rehabilitation system") that can automatically generate quantitative measures of the quality of human motions. The rehabilitation system described herein can automatically recognize a patient's limb motions, as well as provide real-time evaluation and feedback. In some implementations, the rehabilitation system can be a home-oriented cyber-physical system (CPS), which helps patients improve their motion coordination capability via physical training. In other implementations, the rehabilitation system can be employed in medical or clinical environments. The rehabilitation system described herein uses a low-cost thermal camera and pressure sensors to collect the patient's motion data. The motions of the patient's legs and feet are captured by the thermal camera, and the patient's plantar pressure is measured by insole pressure sensors. The rehabilitation system provides quantitative evaluation (e.g., a quantitative measure) of the motions performed by the patient. The quantitative measures include the motion style of the patient's legs, the periodicity of the patient's foot trajectory, and the patient's foot balance level. Also described herein are techniques for extracting the leg skeletons from the thermal images, and for implementing motion signal auto-segmentation, recognition, and analysis of the motion series for the above measures. As described below, experimental results confirm that the example rehabilitation system and techniques can be used to efficiently acquire and analyze lower-limb motion information. Therefore, the example rehabilitation system and techniques can be used for home rehabilitation without the involvement of medical personnel.

Example Rehabilitation Systems

Referring now to FIG. 1A, a block diagram of an example rehabilitation system is shown. The rehabilitation system can include a plurality of sensors 102 for sensing force or pressure exerted by a portion of a subject's body (e.g., at least one of the subject's feet). Additionally and optionally, the rehabilitation system can also include a thermal imaging device 104 (e.g., a thermal camera) for imaging the subject. In some implementations, the rehabilitation system includes either the sensors 102 or the thermal imaging device 104. In some implementations, the rehabilitation system includes both the sensors 102 and the thermal imaging device 104. The rehabilitation system can also include a computing device 200. The computing device 200 is described below with regard to FIG. 2. As described in detail below, the computing device 200 can be configured to receive force or pressure data measured by the sensors 102 or image data captured by the thermal imaging device 104, and calculate a quantitative measure of the subject's limb motion (e.g., a height of raising a limb, a motion cycle similarity score, a quality of periodicity of limb trajectory, or a balance capability of the subject) based on the force or pressure data or the image data. In other words, the computing device 200 can be configured to process the force or pressure data and/or the image data to recognize and evaluate the subject's motion patterns. Optionally, the computing device 200 can also be configured to provide a recommendation for rehabilitation based on the quantitative measure of the subject's limb motion.

As shown in FIG. 1A, the sensors 102 and the thermal imaging device 104 can be communicatively connected to the computing device 200. For example, the sensors 102 and the thermal imaging device 104 can be coupled to the computing device 200 through communication links. This disclosure contemplates the communication links are any suitable communication link. For example, a communication link may be implemented by any medium that facilitates data exchange between the network elements including, but not limited to, wired, wireless and optical links. Alternatively or additionally, the sensors 102 and the thermal imaging device 104 can be coupled to the computing device 200 through one or more networks. This disclosure contemplates that the networks are any suitable communication network. The networks can include a local area network (LAN), a wireless local area network (WLAN), a wide area network (WAN), a metropolitan area network (MAN), a virtual private network (VPN), etc., including portions or combinations of any of the above networks.

In addition, the sensors 102 can be configured to detect a respective pressure or force exerted by each of the subject's feet. For example, the sensors 102 can detect the plantar pressure of both of the subject's feet. As described below, the pressure distribution can be obtained by searching the peak values in the power spectrum of the pressure sensor signals. Optionally, the sensors 102 can be thin-film pressure sensors configured for placement in the subject's footwear (e.g., shoes). In some implementations, a plurality of sensors can be arranged in the subject's footwear (e.g., one or more sensors in each of the subject's shoes). Optionally, as shown in FIG. 1A, the sensors 102 can be communicatively connected to a base station 120 over a wireless communication link. For example, the pressure sensors 102 can transmit pressure or force data to the base station 120 using the ZIGBEE protocol, which is a known, low-power wireless specification (see ZIGBEE specification, available at http://www.zigbee.org/). This disclosure contemplates that the pressure sensors 102 and the base station 120 can communicate using wireless specifications other than ZIGBEE.

Additionally, the base station 120 can be communicatively connected to the computing device 120 using a USB cable, for example. It should be understood that the sensors 102, the base station 120, and the computing device 200 can be coupled using any type of communication link.

The thermal imaging device 104 can be configured to capture images of the subject. The thermal imaging device 104 can obtain a thermal video stream of the subject. Thermal imaging devices have advantages as compared to video cameras described above (e.g., the ability to capture human posture but without the limitations in illumination and/or obstacles because the images are thermal images). For example, the thermal imaging device 104 can optionally capture motion of the subject's limbs such as the subject's lower limbs or legs. Optionally, as shown in FIG. 1A, the thermal imaging device 104 can be communicatively connected to a mobile device 130 (e.g., smart phone, tablet computer, laptop computer, etc.) using a USB cable, for example. THERM-APP of OPGAL OPTRONICS INDUSTRIES LTD. of KARMIEL, ISRAEL is an example thermal imaging device for use with mobile devices. The mobile device 130 can be communicatively connected to the computing device 200 over a wireless link. For example, the mobile device 130 can transmit image data to the computing device 200 using WiFi or BLUETOOTH, which are known wireless technologies. This disclosure contemplates that the mobile device 130 and the computing device 200 can communicate using wireless specifications other than WiFi or BLUETOOTH. It should be understood that the thermal imaging device 104, the mobile device 130, and the computing device 200 can be coupled using any type of communication link.

As shown by dotted box 150 of FIG. 1A, the computing device 200 can be configured to process image data (e.g., thermal images), which was captured by the thermal imaging device 104. For example, as described below, the thermal images can be converted to black and white (B&W) images, the background can be subtracted, and the skeleton model of the subject's lower limbs can then be extracted out from the B&W images for later use. In some implementations, the subject's leg skeleton can be extracted from the image data. In some implementations, the subject's foot or feet skeleton can be extracted from the image data.

Additionally and optionally, the computing device 200 can be configured to segment and recognize similar motions (e.g., normal and/or abnormal walking cycles) within the image data as shown by box 152 of FIG. 1A. Optionally, the computing device 200 can be configured to calculate motion cycle similarity scores (e.g., a quantitative measure of the subject's limb motion). A skeleton and joint extraction technique is described below, which can be used to extract the subject's leg skeleton from the thermal image data. In addition, an enhanced Dynamic Time Warping (DTW) technique, called Peak Match Time Warping (PMTW), is described, which can process extracted leg skeleton data for accurate recognition and auto-segmentation of the motion series. The PMTW technique uses peaks in the signal for changing point detections in the structure of the motion series. It matches the peaks of time series first, and then aligns all series based on the matched peaks. The similarity of the peak appearance patterns can then be calculated, so that different phases of the motion series can be identified and compared. The PMTW technique significantly reduces the computation time during the optimal warping path search, compared to the DTW technique. Additionally, the PMTW technique can avoid mismatches between the time series containing peaks. Further, the PMTW technique requires no data filtering and can remove small peaks below a preset threshold. This guarantees its strong ability to resist data noise. The PMTW technique is also not sensitive to the speed of motions. The PMTW-based segmentation uses template series for segmentation, and finds all the matched segments in a long testing series (e.g., the image data) based on the template series.

Additionally and optionally, the computing device 200 can be configured to calculate a quality of periodicity of limb motion (e.g., a quantitative measure of the subject's limb motion) as shown by box 154 of FIG. 1A. In other words, a periodicity detection technique is described below. A skeleton and joint extraction technique is described below, which can be used to extract the subject's foot or feet skeleton from the thermal image data. In addition, an enhanced Time-Delay Embedding (TDE) technique, called Scored Time-Delay Embedding (STDE), is described, which can process extracted feet skeleton data in order to find the periodicity of the motion series. The STDE technique described herein automatically generates a score for different periodicity degrees. In physical training, the evaluation of periodicity of motion is very important since a disabled subject cannot easily guarantee the same pattern during each motion repetition. Thus, by quantitatively measuring the times that a subject can successfully repeat a desired action, it is possible to assess the progress of the rehabilitation.

As shown by dotted box 160 of FIG. 1A, the computing device 200 can be configured to process force or pressure data, which was detected by the pressure sensors 102. Optionally, the computing device 200 can be configured to calculate a balance capability of the subject (e.g., a foot balance measurement), as shown by box 162 of FIG. 1A. For example, the sensors 102 can detect the plantar pressure of both of the subject's feet. As described below, the pressure distribution can be obtained by searching the peak values in the power spectrum of the pressure sensor signals. Discrete Fourier Transform can be used to obtain the power spectrum of the plantar pressure. The distribution of plantar pressure can provide the foot balance status of the subject, which is also an important rehabilitation progress metric.

Figure 1B:
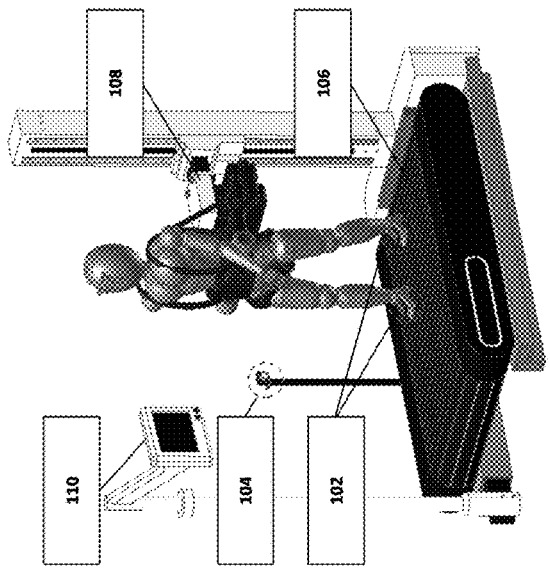
FIG. 1B is a perspective view of an example rehabilitation system.

Referring now to FIG. 1B, a perspective view of an example rehabilitation system according to an implementation described herein is shown. In some implementations, the example rehabilitation system can be located outside of a medical environment, e.g., in the subject's home. In some implementations, the example rehabilitation system can be located in a medical environment, e.g., in a hospital or physical therapy center. The rehabilitation system can include a plurality of pressure sensors 102, a thermal imaging device 104, and a computing device (not shown in FIG. 1B). These features are described above with regard to FIG. 1A and therefore not described in further detail with regard to FIG. 1B. Optionally, as shown in FIG. 1B, the rehabilitation system can include an assistive walking device 106 such as a treadmill, for example. Additionally, the rehabilitation system can include a supporting arm 108, which is configured to support the subject during rehabilitation activities involving the assistive walking device 106. The rehabilitation system can also optionally include a display device 110, which can be communicatively connected to the computing device (e.g., computing device 200 of FIG. 1A) using any type of communication link. The display device 110 can be used to provide visual feedback to the subject during rehabilitation exercises. This disclosure contemplates that the feedback is not limited to visual feedback, and the feedback can include, but is not limited to, visual, audible, or tactile feedback. Additionally and optionally, the computing device can be configured to generate an instruction related to the subject's limb motion based on the quantitative measure (e.g., a height of raising a limb, a motion cycle similarity score, a quality of periodicity of limb trajectory, or a balance capability of the subject), and the instruction can be transmitted to and graphically displayed on the display device 110. For example, the instruction can optionally be a recommended change in: a height of limb motion, a direction of limb motion, a speed of limb motion, or a placement of the subject's foot.

Figure 2:
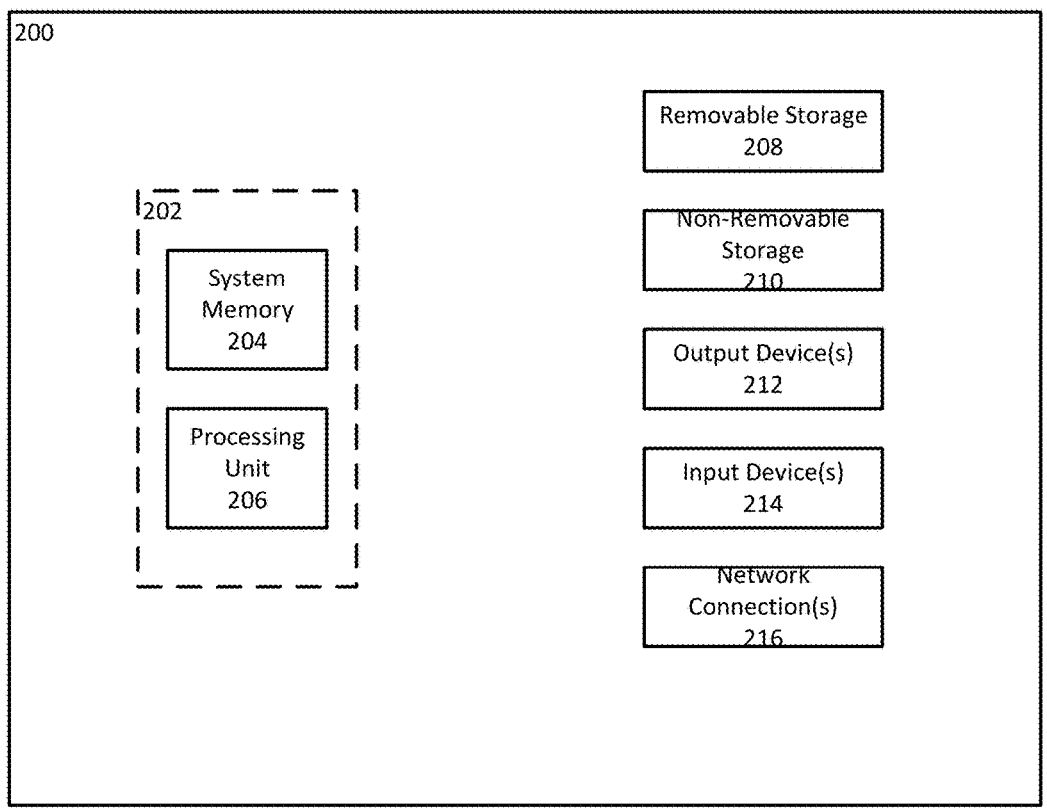
FIG. 2 is an example computing device.

Referring to FIG. 2, an example computing device 200 upon which embodiments of the invention may be implemented is illustrated. It should be understood that the example computing device 200 is only one example of a suitable computing environment upon which embodiments of the invention may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Image Processing and Limb Motion Analysis

It should be appreciated that the logical operations described herein with respect to the various figures may be implemented (1) as a sequence of computer implemented acts or program modules (i.e., software) running on a computing device (e.g., the computing device described in FIG. 2), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Motion signal segmentation is an important step since atom actions must be extracted from the thermal image data. Known algorithms exist that use simple signal features for the segmentation of motion series. For example, in the works that used inertial sensors (I. P. I. Pappas, T. Keller, S. Mangold, M. R. Popovic, V. Dietz, M. Morari, "A reliable gyroscope-based gait-phase detection sensor embedded in a shoe insole," IEEE Sensors Journal, vol. 4, no. 2, pp. 268-274, April 2004; Y. L. Hsu, P. C. Chung, W. H. Wang, M. C. Pai, C. Y. Wang, C. W. Lin, H. L. Wu, J. S. Wang, "Gait and Balance Analysis for Patients With Alzheimer's Disease Using an Inertial-Sensor-Based Wearable Instrument," IEEE Journal of Biomedical and Health Informatics, vol. 18, no. 6, pp. 1822-1830, November 2014; S. R. Hundza, W. R. Hook, C. R. Harris, S. V. Mahajan, P. A. Leslie, C. A. Spani, L. G. Spalteholz, B. J. Birch, D. T. Commandeur, N. J. Livingston, "Accurate and Reliable Gait Cycle Detection in Parkinson's Disease," IEEE Trans. Neural Syst. Rehabil. Eng., vol. 22, no. 1, pp. 127-137, January 2014; W. Lee, S. Yen, A. Tay, Z. Zhao, T. M. Xu, K. K. M. Ling, Y. Ng, E. Chew, A. L. K. Cheong, and G. K. C. Huat, "A Smartphone-Centric System for the Range of Motion Assessment in Stroke Patients," IEEE Journal of Biomedical and Health Informatics, vol. 18, no. 6, pp. 1839-1847, November 2014) and insole pressure sensors (A. M. Howell, T. Kobayashi, H. A. Hayes, K. B. Foreman, S. J. M. Bamberg, "Kinetic Gait Analysis Using a Low-Cost Insole," IEEE Trans. Bio. Eng., vol. 60, no. 12, pp. 3284-3290, December 2013; V. Agostini, G. Balestra, M. Knaflitz, "Segmentation and Classification of Gait Cycles," IEEE Trans. Neural Syst. Rehabil. Eng., vol. 22, no. 5, pp. 946-952, September 2014), the gait parameters are estimated and the gait cycles are segmented by examining the changing points of the sensor signals.

Some other works have used more accurate segmentation and recognition methods. For example, Lin et al. have proposed an online segmentation scheme by using zero-velocity crossings (ZVC) and velocity peaks as features. J. F.-S. Lin, D. Kulic, "Online Segmentation of Human Motion for Automated Rehabilitation Exercise Analysis," IEEE Trans. Neural Syst. Rehabil. Eng., vol. 22, no. 1, pp. 168-180, January 2014. These features serve as the exemplars for Hidden Markov Model (HMM), and then the time series are recognized and segmented by HMM. Lin's method has applied a frequency filter to the signal, and can thus filter out the fast or slow motions. Frank et al. have used Time-Delay Embedding (TDE) method to recognize the time series. TDE projects the 1-dimension inertial signals to a 3-dimension phase space, and implements the recognition in the phase space. J. Frank, S. Mannor, J. Pineau, D. Precup, "Time Series Analysis Using Geometric Template Matching," IEEE Tran. Pattern Analysis and Machine Intelligence, vol. 35, no. 3, pp. 740-754, March 2013. Frank's method is easy for implementation but loses too much information of the motion series due to its over-simplified features (i.e., just using one parameter called attractor).

Another method for recognition or matching the time series is Dynamic Time Warping (DTW). It can calculate the similarity between two time series with different lengths, but the DTW alignment of two time series only considers the amplitudes of series. Thus, DTW can sometimes match points with close amplitudes together, even when one point is at the peak and the other is at the valley. The mismatched point results in poor singularity.

Keogh et al. have proposed a Derivative Dynamic Time Warping (DDTW), which alleviates the above-mentioned mismatch problem of DTW by introducing the first order derivative of the time series. E. J. Keogh and M. J. Pazzani, "Derivative dynamic time warping," SIAM Int. Conf. on Data Mining (SDM), pp. 1C11, 2001. Shimodaira et al. have developed a Dynamic Time-Alignment Kernel method (DTAK), which is a kernel DTW used in support vector machine (SVM). H. Shimodaira, K.-I. Noma, M. Nakai, and S. Sagayama, "Dynamic Time-Alignment Kernel in Support Vector Machine," Proc. Neural Information Processing Systems, 2001. These variations of DTW are universal in many problems, but still have large uncertainty in seeking the similarity between the time series. Zhou et al. have developed a hierarchical segmentation based on DTAK and k-means clustering. F. Zhou, F. D. Torre, and J. K. Hodgins, "Hierarchical Aligned Cluster Analysis for Temporal Clustering of Human Motion," IEEE Tran. Pattern Analysis and Machine Intelligence, vol. 35, no. 3, pp. 582-596, March 2013. It can be applied to all kinds of human skeleton data or images. Zhou's method uses an unsupervised learning. However, Zhou has large computation overhead and is sensitive to initial values and parameters. Gong et al. proposed a segmentation and recognition method based on spatial-temporal alignment. D. Gong, G. Medioni, X. Zhao, "Structured Time Series Analysis for Human Action Segmentation and Recognition," IEEE Tran. Pattern Analysis and Machine Intelligence, vol. 36, no. 7, pp. 1414-1427, July 2014. It is validated on skeleton data and depth sensor data. Gong uses degree of completion as the feature for segmentation, and aligns the motion series in both temporal and spatial domains. This method is good at recognizing very different motions, but may not have strong discrimination among similar motions in rehabilitation training.

Liu and Picard have used spectrum power of Fourier Transform to determine the periodicity of an image series. F. Liu, R. W. Picard, "Finding periodicity in space and time," Sixth International Conference on Computer Vision, pp. 376-383, January 1998. However, the Fourier spectrum power can only determine the existence of sinusoid components, and thus is not a good measure of periodicity if the motion signals do not have significant sinusoid patterns. There are two methods that can visually reveal the periodicity of a time series, i.e., recurrent plot and Time-Delay Embedding (TDE). Recurrent plot can show the periodicity in a 2-D matrix, and TDE can reveal the periodicity in a 3-D space. The TDE reconstruction forms an attractor, which is a closed set of data.

Quantitative Measures of Limb Motion

American Physical Therapy Association (APTA) has defined 54 outcome measures covering body structure and function, as well as activities for patients with stroke in rehabilitation. Post Stoke rehabilitation effect measurement, available at: http://www.neuropt.org/professional-resources/ neurology-sectionoutcome-measures-recommendations/ stroke. The measures such as "6 minute walk", "5 time sit to stand", and "Berg Balance Scale", etc., are assessments of the patient's speed, strength, endurance, etc. However, these measures are mostly single-value definitions of the final training effects without measures of the entire training process (e.g., during physical training). For example, these measure do not show how many times a patient raises his leg above a certain height, whether the patient's motion shows good periodical patterns, etc. On the other hand, the quantitative measures described herein reveal the dynamics of the patient's motions, even within a rehabilitation training session.

For example, the rehabilitation system can be configured calculate a quantitative measure of the subject's limb motion. Examples quantitative measures are described below and can include, but are not limited to, a height or trajectory of raising a limb, a motion cycle similarity score, a quality of periodicity of limb motion, and a balance capability of the subject (e.g., a foot balance measure). The limb can optionally be the subject's lower limb (e.g., leg). It should be understood, however, that although examples of lower-limb rehabilitation are described herein, the techniques can also be used for other detections such as upper-limb motion patterns.

Height or trajectory of raising a limb. Jaffe et al. found that the individuals with post-stroke hemiplegia have an obvious improvement in gait velocity and endurance by taking the training of stepping over obstacles. D. L. Jaffe, D. A. Brown, C. D. Pierson-Carey, E. L. Buckley, and H. L. Lew, "Stepping over obstacles to improve walking in individuals with poststroke hemiplegia" Journal of Rehabilitation Research & Development, vol. 41, no. 3A, pp. 283-292, May-June 2004. As a matter of fact, raising legs is not a simple training step. It requires good coordination and enough strength for most of the leg muscles. Therefore, the rehabilitation system can be configured to measure the height of the raising legs accurately through the thermal image processing.

Quality of periodicity of limb motion. The repeatability of the motion trajectory is considered as an important measure of the patient's ability to control the limbs. For normal (e.g., non-disabled) people, it takes no effort to repeat walking cycles. But for the stroke patients (e.g., disabled), it is already difficult for them to move the limbs, not to mention move with the same pattern each time. By training stroke patients to walk with high repeatability, it is possible to help them improve the control of the leg muscles. Therefore, the rehabilitation system can be configured to calculate a measure of periodicity of limb motion.

Balance capability of the subject. For this measure, the distribution of the plantar pressure is the focus. The imbalance of pressure between two feet can be detected using the pressure sensors (e.g., the pressure sensors 102 of FIGS. 1A and 1B) of the rehabilitation system. Additionally, the pressure distribution within a single foot can tell which part of the foot the subject intends to use, e.g., inside foot, outside foot, front foot, or heel. These parameters are helpful to correct the patient's gait. Therefore, the rehabilitation system can be configured to calculate a foot balance measure.

The motion analysis of the lower limbs is composed of three parts: (1) recognition and segmentation of the motion data series, (2) quantification of the periodicity of the motion trajectory, and (3) foot balance analysis. As described below, (1) and (2) use skeleton data extracted from the thermal image data (e.g., captured by the thermal imaging device 104 of FIGS. 1A and 1B) and (3) uses the plantar force or pressure data (e.g., detected by the pressure sensors 102 of FIGS. 1A and 1B).

Skeleton Extraction from Thermal Image

Figure 3A:
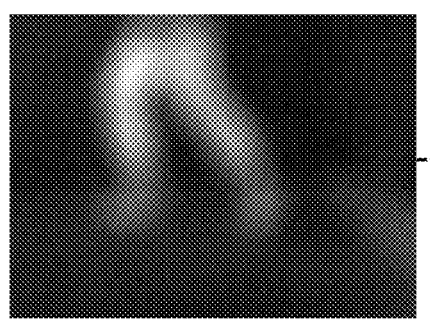
FIGS. 3A-3D illustrate the process of extracting the skeleton image of lower limbs from a thermal image of a subject.
Figure 3B:
Figure 3C:
Figure 3D:
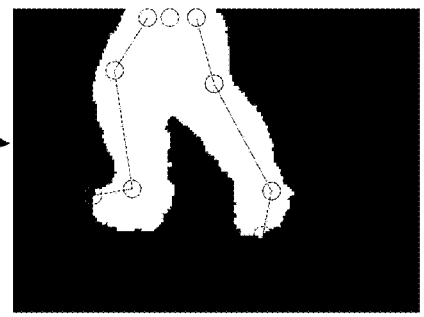

Unlike video cameras or depth sensors (e.g., MICROSOFT KINECT), a thermal camera only detects warm/hot targets. It is therefore possible to subtract the background using noise reduction techniques. It is possible to do so even when there are obstacle(s) around the subject. FIGS. 3A-3D illustrate the process of extracting the skeleton image of the subject's lower limbs from a thermal image of the subject. The raw thermal image is shown in FIG. 3A. The B&W thermal image is shown in FIG. 3B. Noise reduction is applied, and the resulting image is shown in FIG. 3C. FIG. 3D illustrates the extracted skeleton. The accuracy of the skeleton model determines the recognition accuracy of the motions.

Since a complicated algorithm is not desired for use in a real-time rehabilitation system, a fast skeleton extraction algorithm for application to the B&W thermal images can be applied. The skeleton extraction algorithm is based on segmented linear regression. The algorithm includes two steps: (1) First, the edge of the extracted subject is taken out as a curve to be processed. (2) Second, the curve is scanned through to find the changing points. The curve is fitted by the segmented straight lines based on the detected changing points. FIG. 4 is a graph illustrating the segmented linear regression of the edge of the subject's leg. These changing points (e.g., the circles in FIG. 3D) are actually the skeleton joints of the leg. They are determined by the minimum error between the curve and the segmented lines.

The overall error function is given by Eq. (1):

$$ERR = \sum_{i=1}^{n} (1 - w_i) \times MSE_i + w_i / l_i, \tag{1}$$

where $w_i$ is the weighting factor, MSE is the mean square error, and $l_i$ is the length of the segmented line. n is the number of segments. In FIG. 3D, there are four segmented lines, thus n=4. The objective function minimizes the overall error by choosing the weighted $MSE_i$ and $l_i$.

It is possible to set up the value of $l_i$ based on certain prior knowledge. For example, if the range of length between skeleton joints is known, it is possible to set up the value of $l_i$ in this range and assign a relatively large weighting to it, such that the objective function can converge quickly. It should be understood that the above technique can be used not only for skeleton extraction of human legs, but also for other parts of the human body or other non-human subjects. The resolution of the skeleton model can be adjusted by changing the number of the segmented lines n. More lines result in more skeleton joints and smaller skeletons.

Motion Recognition

Recognition of the motion series can be performed based on the extracted lower limb skeleton data (as described above). Two problems need to be solved to recognize the motion series: (1) calculating the similarity between different motion series; and (2) segmentation of the motion series. Using techniques described herein, it is possible to recognize similar motion series and/or similar motion cycles with a motion series (e.g., using a motion cycle similarity score). For example, the similarity between different postures can be derived from the coordinates of the extracted skeleton data.

It should be understood that a motion series can include different postures and may have different lengths. A motion series is contained in, or can be derived from, the image data captured by the thermal camera (e.g., the thermal imaging device 104 of FIGS. 1A and 1B). Optionally, a plurality of motion series can be contained in, or derived from, a continuous time segment of the image data. For example, a motion series can define the subject's limb motion in at least one dimension. In some implementations, a motion series defines the movement of the subject's limb motion (e.g., a particular joint) in one dimension (e.g., the x-, y-, or z-dimension). In some implementations, a motion series defines the movement of the subject's limb motion (e.g., a particular joint) in two dimensions (e.g., two of the x-, y-, and z-dimensions). In some implementations, a motion series defines the movement of the subject's limb motion (e.g., a particular joint) in three-dimensional space (e.g., the x-, y-, and z-dimensions).

Using conventional methods, it can be challenging to determine (and much less quantify) the similarity between motion series having different lengths. In particular, it is possible to either extract some features from the motion series or directly compare the raw data of two motion series. However, using extracted features for recognition may lose important information if the selected features are not intrinsic to motion analysis. A known method to calculate the similarity between two series with different lengths is DTW. Using DTW, it is possible to calculate a similarity matrix for the two series, and then search for an optimal warping path with the maximal cumulative similarity. For example, FIGS. 5A and 5B illustrate an example of DTW alignment (FIG. 5A) and the warping path of DTW in the cumulative similarity matrix (FIG. 5B). DTW only considers the similar values in the series, and typically ignores the temporal characteristics of the series.

Motion Cycle Similarity Score

A Peak Matching Time Warping (PMTW) method is described below. It should be understood that the PMTW method can be applied to any time series, including but not limited to a motion series. The PMTW method can determine, as well as provide a quantitative measure of, the similarity between time series. This includes recognizing normal and/or abnormal walking cycles within a motion series. Most human motions contain periodical patterns. These series are composed of positive and negative peaks. The PMTW method can calculate the similarity between two time series. The series alignment in PMTW is based on the matching of the peaks. Accordingly, PMTW avoids DTW's singularity and mismatching issues, and also avoids the search of the optimal warping path.

Finding Peaks:

The time series with noise typically contains small peaks everywhere. A frequency filter can be used to eliminate the noise. However, a frequency filter may not be efficient in rehabilitation applications because human motions may have slow or fast motions, and they could have the same frequency as the noise. In the motion data, an efficient way to determine whether the signal is noise is to check its amplitudes. Thus, an amplitude smoothing method can be used to get rid of the noise and find the peaks with large amplitudes.

Figure 6:
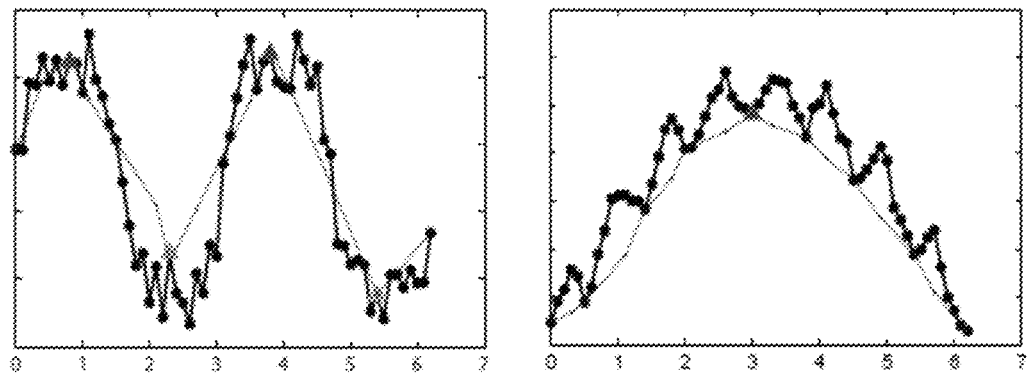
FIG. 6 illustrates two examples of detecting peaks using the amplitude smoothing method described herein.

First, amplitude smoothing includes detecting all the peaks (including the noise) in the motion series. Second, if the amplitude of a peak is under a threshold, its amplitude is replaced by the average of its neighboring two peaks. The averaging operation is implemented iteratively until the amplitudes of all peaks are above the threshold. It should be understood that the computation load of each iteration will be half of the last iteration. It has been shown that at most 5 iterations of computation is enough to eliminate all of the noise. And, the computational cost of amplitude smoothing with 4 iterations is the same as the scheme of using discrete Fourier transform for the same series. FIG. 6 illustrates two examples of detecting peaks using amplitude smoothing.

Figure 7A:
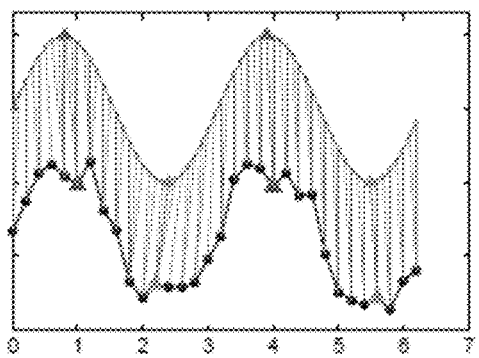
FIGS. 7A and 7B illustrate PMTW alignment of two time series.
Figure 7B:
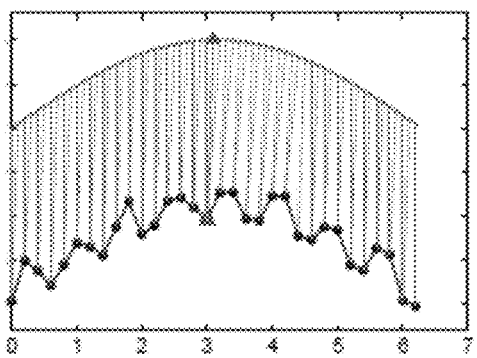
Figure 7C:
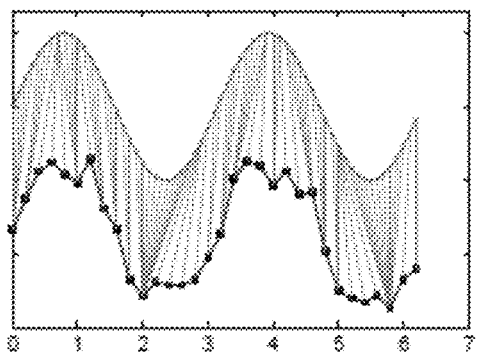
FIGS. 7C and 7D illustrate DTW alignment of the same time series aligned in FIGS. 7A and 7B.
Figure 7D:
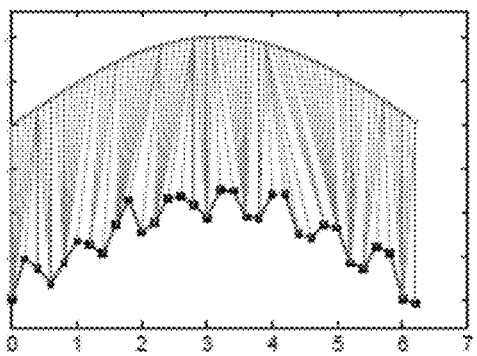

Matching the Peaks and Warping the Series:

All of the peaks obtained in last step can be matched. And, the rest of points in the series can be equally aligned between the neighboring two peaks. FIGS. 7A and 7B illustrate PMTW alignment of two time series. FIGS. 7C and 7D illustrate DTW alignment of the same time series aligned in FIGS. 7A and 7B. PMTW does not require searching the optimal path because the main structure of the warping has already been determined by the matched peaks.

Figure 8A:
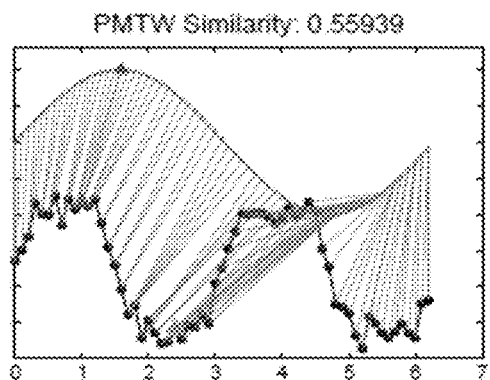
FIGS. 8A-8D illustrate the comparison between PMTW and DTW based similarity calculations for two motion series.
Figure 8B:
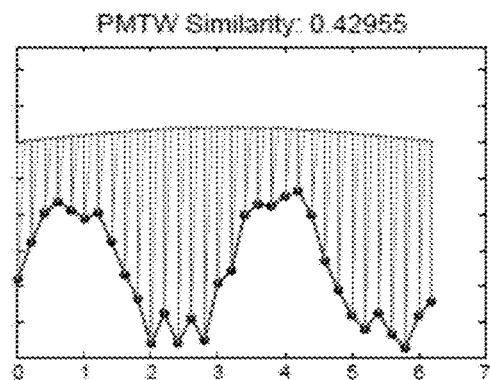
Figure 8C:
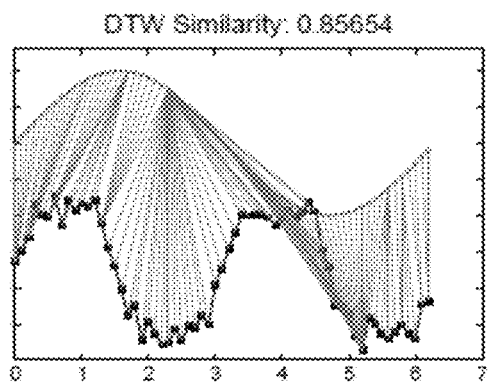
Figure 8D:
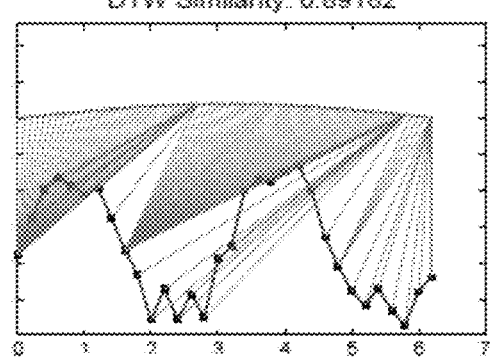

If a time series (e.g., a tested motion series) has a different peak pattern from a template series (e.g., either different number of peaks or different orders of positive/negative peaks), the unmatched peaks can be aligned to the end of the series. Comparing to DTW, PMTW can align the unmatched peaks to similar values without the need of considering the structure of the series. Thus, PMTW can obtain a smaller distance than DTW between two series that have different peak patterns. FIGS. 8A-8D illustrate the comparison between PMTW and DTW based similarity calculations for two motion series. In FIGS. 8A and 8B, since PMTW cannot find the matched peaks, it gives a low similarity score. However, in FIGS. 8C and 8D, DTW attempts to align the testing points with their similar counterpoints, even though the alignment is totally wrong. This results in a high similarity score by mistake between two dissimilar series. Therefore, using DTW to recognize motion series can sometimes generate wrong matching results.

Motion Feature Space:

A motion series (e.g., including a normal and/or abnormal walking cycles) can be recognized through the analysis of peaks of the motion series using the PMTW method described herein. To achieve a more convenient observation of the human motion series, a feature space can be constructed based on the peak pattern of time series. The peak pattern can include an amplitude, order, or speed of peaks.

This feature space provides a natural classification of time series from the aspects of the amplitude, the order of peaks, and the speed. The zero point of this space is the series with zero amplitude.

The amplitude of a series in this space is the PMTW distance between the series and the zero series.

$$\text{Amplitude} = D_{PMTW}(s_i, s_0), \tag{2}$$

The order of peaks is the temporal order of positive and negative peaks, denoted as (+−+−++ . . . ).

The speed of a series in this space is the number of peaks divided by the number of points.

$$\text{Speed} = \frac{Number of \text{ peaks}}{Length of \text{ series}}, \tag{3}$$

Figure 9:
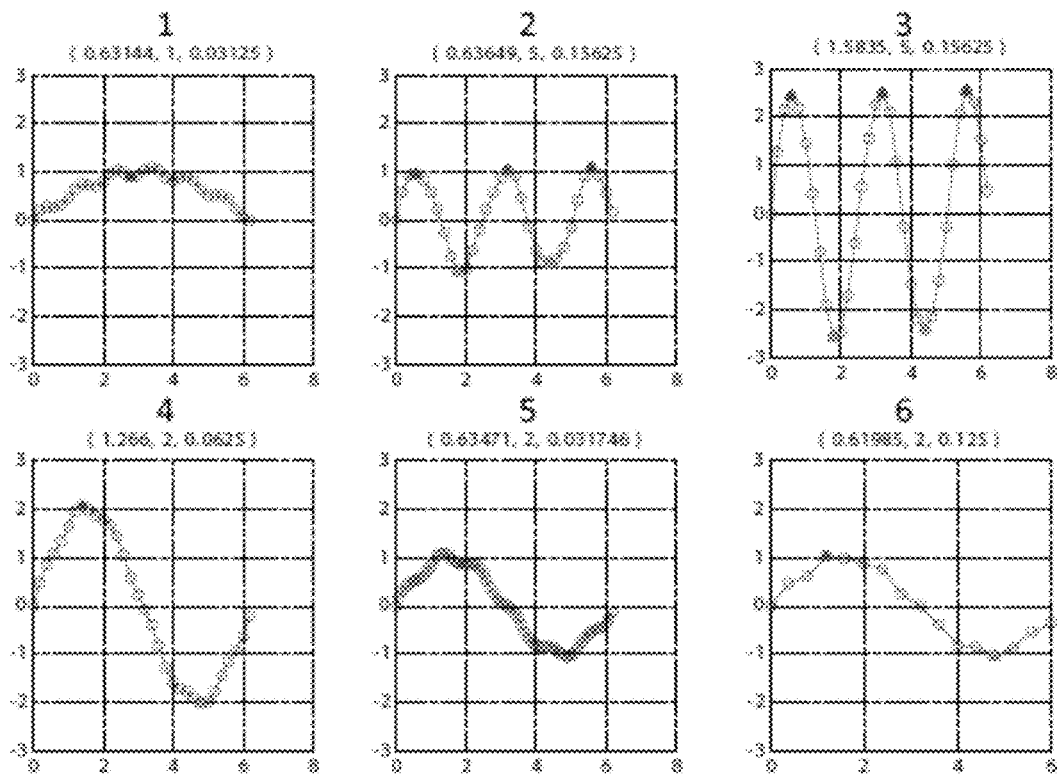
FIG. 9 illustrates examples of the feature vector for a number of time series in the 3-dimensional (3D) space.
Figure 10A:
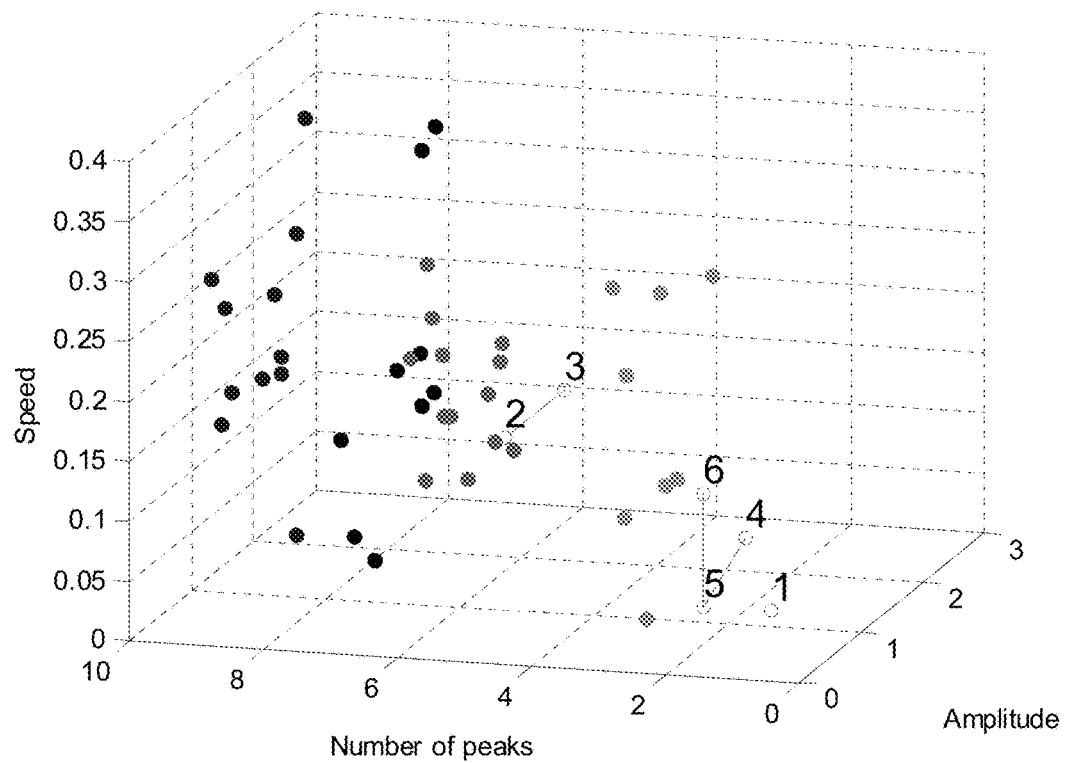
FIG. 10A is a representation of time series in the peak feature space.
Figure 10B:
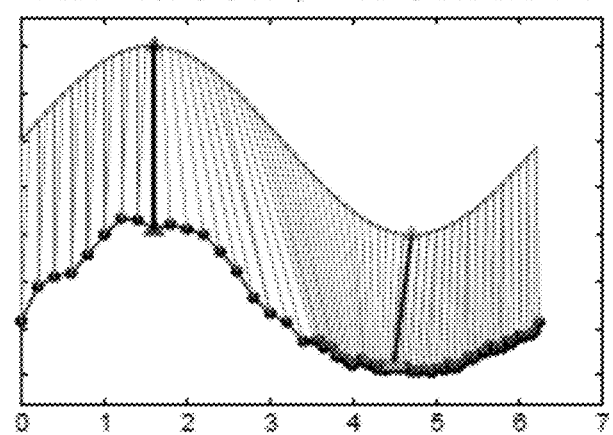
FIG. 10B illustrates the comparison of each peak of the tested motion series.

FIG. 9 illustrates examples of the feature vector for a number of time series in the 3-dimensional (3D) space. In FIG. 9, the order of peaks is replaced by the number of peaks for easier understanding. FIG. 10A is a representation of time series in this peak feature space. Different shaded dots indicate time series with different numbers of peaks, and the labeled points (1-6) represent the time series shown in FIG. 9. The dimension of the order of peaks is actually larger than one. FIG. 10B illustrates the comparison of each peak of the tested motion series.

Through the peak feature space based on PMTW method, the following facts of the time series can be observed:
  if the peak patterns are matched;
  if the amplitudes of the matched peaks are similar;
  if the speeds are similar.

Furthermore, it is possible to compare the amplitude and speed of each peak, so that a subject can be advised in which part he/she can improve. For the example, as shown in FIG. 10B, the subject can be notified (e.g., using the display device 110 of FIG. 1B that he/she is doing well in the first half cycle (e.g., Score 0.994), but needs larger amplitude and faster speed in the second half cycle (e.g., Score 0.443). Optionally, the feature space can be an orthogonal space and each motion series can be uniquely mapped to a point in this space. From manifold point of view, the time warping method such as DTW could be treated as a mapping model that projects the time series to another one with the same length as its peer. Unfortunately, most of the time warping methods only try to map the series to each other rather than map them uniquely. On the other hand, the PMTW method described herein can seize the main structure of the time series, i.e., the peak pattern, thus the PMTW can map a series to a more unique feature point, as shown in Equation 4, where $A_i, P_i, S_i$ indicate the amplitude, the order of peaks, and speed, respectively. The feature space may not be orthogonal and has no unique mapping for the motion series, but it can well explain the intrinsic features of the human motions.

$$F_i = M_{PMTW}(s_i) = (A_i, P_i, S_i), \quad (4)$$

Segmentation of Motion Series:

The segmentation of a time series based on PMTW is a supervised learning process. It finds the segments with matched peaks and high similarity as compared to a template series. Optionally, the template series can be used to identify normal walking cycles within the motion series. A series that is not matched with the template series will not be recognized.

Figure 11:
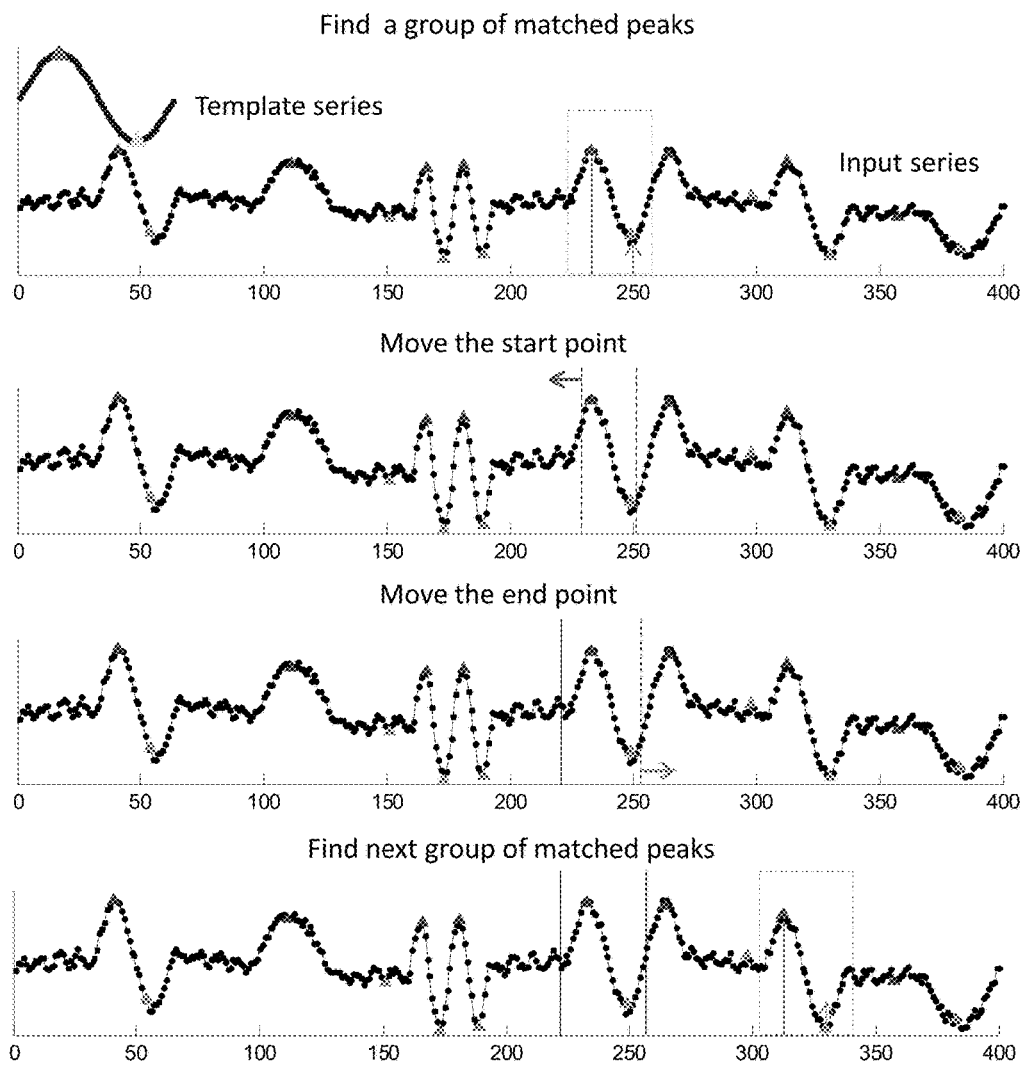
FIG. 11 illustrates the method for segmenting an input series (e.g., a time series such as a motion series) given a template series.

FIG. 11 illustrates the procedure for segmenting an input series (e.g., a time series such as a motion series) given a template series. The input series contains segments that have matched peaks with the template series, and the segmentation starts from the beginning and moves to the end of the input series to find all the matched segments, based on the following main steps:

1. Find all the peaks in the input series.
2. Locate the first group of matched peaks.
3. Initialize the starting point and ending point. Set starting point at the first matched peak, and ending point at the last matched peak.
4. Move starting point backward until encountering the previous peak, and then calculate the PMTW score. Pick the point with the largest score as the final starting point.
5. Move the ending point forward until seeing the next peak, and calculate the PMTW score. Pick the point with the largest score as the final ending point.
6. Go forward to search for the next group of matched peaks.

Figure 13:
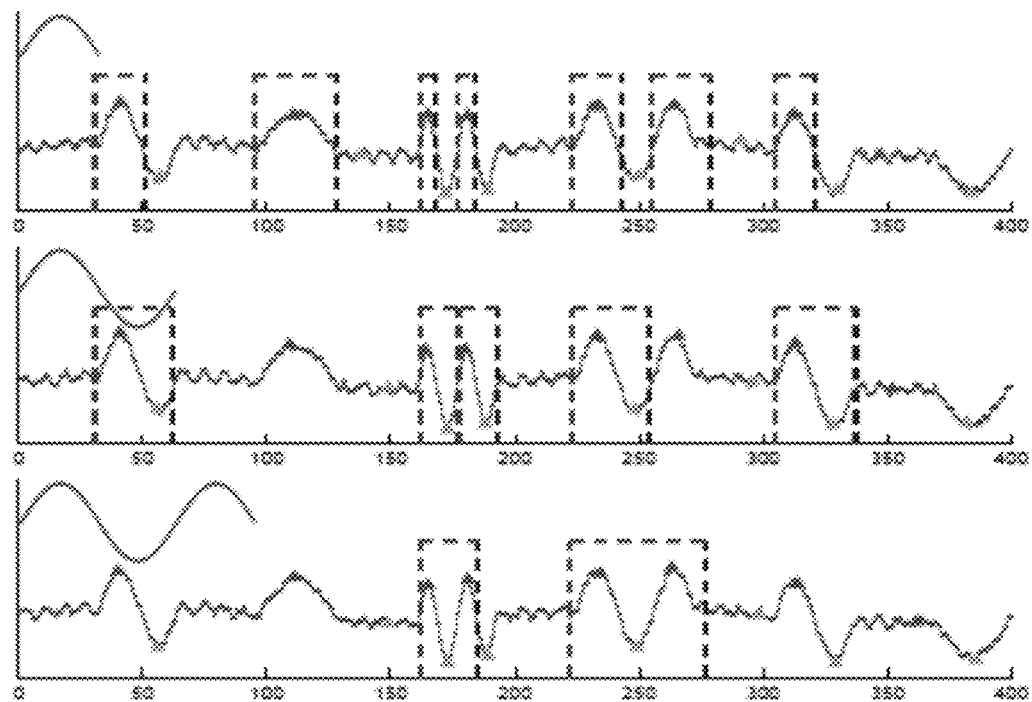
FIG. 13 illustrates an example of the segmentation of a long synthetic series containing different patterns of peaks using PMTW.

FIG. 12 is the algorithm that implements the segmentation based on PMTW given in pseudo codes. The input variables of the algorithm are the template series $s_t$ and the tested long series $s_i$, and the output is the segmentation positions seg_point. FIG. 13 illustrates an example of the segmentation of a long synthetic series containing different patterns of peaks using PMTW. The segmented portions are shown in dotted boxes. It can be seen that the series matched with different templates are recognized and segmented from the long series. These series are recognized even they are disturbed by noise and have very different speeds from the templates.

Accordingly, the PMTW method described above can be used to segment a time series. This disclosure contemplates that the time series is not limited to the motion series described in the examples herein. It should be understood that the PMTW method can optionally be implemented using a computing device (e.g., the computing device 200 of FIG. 2). The method can include receiving a signal, identifying one or more peaks within the signal, matching a peak pattern of the signal to a peak pattern of a template signal, and calculating a similarity score between one or more peaks within the signal and one or more peaks within the template signal. A portion of the signal can be segmented based the similarity score. Optionally, the peak pattern can be an amplitude, order, or speed of peaks.

In some implementations, the PMTW method described above can be used to recognize normal and/or abnormal motion cycles within a motion series. The motion series can be extracted from the image data captured by a thermal camera (e.g., the thermal imaging device 104 of FIGS. 1A and 1B). It should be understood that the PMTW method can optionally be implemented using a computing device (e.g., the computing device 200 of FIG. 2). The method can include a comparison between a peak pattern of the motion series and a peak pattern of a template motion series (e.g., a series that defines a normal motion cycle). The method can further include recognizing an abnormal motion cycle within the motion series based on a comparison between a peak pattern of the motion series and a peak pattern of a template motion series. Additionally and optionally, the quantitative measure of the subject's limb motion can be calculated as a motion cycle similarity score (e.g., the PMTW score) between one or more peaks within the motion series and one or more peaks within the template motion series.

Quality of Periodicity of Trajectory

The quality of the periodicity of motion trajectory is an effective measure of the rehabilitation performance. A well-recovered patient can repeat an expected action again and again. And, there is consistent style in leg movements. For example, each walking length should be the same for a well-recovered patient.

Regarding the period detection, a Fourier Transform based method can be used. However, the Fourier Transform based frequency analysis can only find out whether the time series contains sinusoid signals. A sinusoid signal with only one period will have a large amplitude in its Fourier Transform. Therefore, Fourier Transform cannot accurately measure the quality of periodicity. Both recurrence plot and Time-Delay Embedding (TDE) can visualize the periodicity of the time series in a 2-D matrix or 3-D space, but a quantitative measuring method is expected to measure the degree of repeatability.

TDE-Based Method:

TDE is a technique of reconstructing the dynamics of time series. Suppose there is a dynamical system whose state at time t is $s_t \in R^d$, and all the possible states of the system belong to the phase space. These states cannot be directly measured, and the dimension of the phase space d is also unknown. But, given the observation of the system $o_t = \alpha(s_t) \in R$, where $\alpha$ is a smooth observation function. TDE can reconstruct the states $s_t$ by using $o_t$.

Takens Embedding Theorem states that a manifold $M \subset R^d$ can be embedded by the time-delay coordinates with lag $\tau$ in a k-dimensional space, if $\tau$ does not conflict with the period of $o_t$ and k>2 m, as shown in Eq. 5. F. Takens, "Detecting strange attractors in turbulence," Dynamical Systems and Turbulence, Warwick 1980, vol. 898, no. 3, pp. 366-381, 1981.

$$\varphi(s_t) = [x(s_t), x(s_{t-\tau}), \ldots, x(s_{t-(k-1)\tau})], \quad (5)$$

The smooth map $\varphi M \to R^k$ for an embedding indicates that it preserves the local structure. In dynamic systems, an attractor is a closed subset of the states towards which the system will evolve from a wide variety of initial conditions. This attractor $A \subset R^d$ can be treated as a manifold in the phase space. According to Takens Theorem, the attractor A can be embedded by:

$$f(s_t) = [\alpha(s_t), \alpha(s_{t-\tau}), \ldots, \alpha(s_{t-(k-1)\tau})] \quad (6)$$
$$= [o_t, o_{t-\tau}, \ldots, o_{t-(k-1)\tau}],$$

where $s_t \in A$. So the embedding k-dimension delay-vector $[o_t, o_{t-\tau}, \ldots, o_{t-(k-1)\tau}]$ is a reconstruction of the attractor A. FIGS. 14A-14F illustrate the TDE reconstruction of some common 1-D time series (i.e., sinusoid, sinusoid with noise, sawtooth, synthetic sinusoid, complicated synthetic sinusoid, and random signal, respectively) in 3-D space. As shown, the series with simple cycles and high repeatability have a simple and closed attractor, while the random signal has no attractor but a mess.

Scored Time-Delay Embedding Method:

The TDE method can help to observe the periodicity of the time series, but it does not provide a way to quantitatively measure the periodicity. Utilizing the attractor found by TDE, an improved TDE method, which better defines the periodicity of the time series, is described below. It calculates the convergence or simplicity of the attractor, and determines a score for the periodicity. By observing the TDE of the signals shown in FIGS. 14A-14F, some conclusions can be drawn: (a) the more periodic the series is, the shorter length the attractor has; (b) the more periodic the series is, the more likely the points of the attractor lie in the same place. Based on these the above two observations, an algorithm can be developed to calculate the repeatability of the time series, that is, it is possible to calculate the linear density of shortest path in the attractor. Optionally, the quantitative measure can be the quality of the periodicity of limb trajectory described herein. An enhanced TDE method, called Scored TDE (STDE), to achieve such a calculation is described below. Its procedure is as follows:

1. Calculate the TDE of the time series.
2. Pick any point of the attractor as the starting point.
3. Select the nearest neighbor of the starting point as the second point.
4. Repeat the same steps to select the third point and the rest of points. Note that the points that have been selected cannot be used twice.
5. Calculate the linear length $L_s$ of the generated shortest path.
6. Calculate the quality of periodicity:

$$Q_{STDE} = \frac{Number of \text{ Points}}{L_s}, \quad (7)$$

Figure 15:
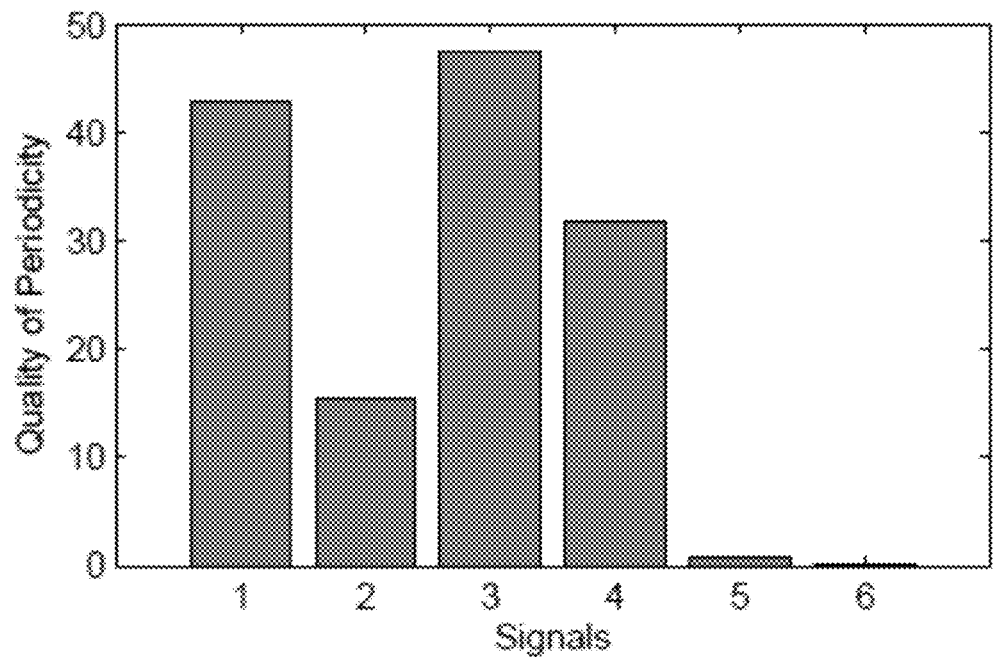
FIG. 15 illustrates the quality of periodicity based on the STDE method for the signals of FIGS. 14A-14F (i.e., 1—sinusoid, 2—sinusoid with noise, 3—sawtooth, 4—synthetic sinusoid, 5—complicated synthetic sinusoid, and 6—random signal, respectively).

The purpose of calculating the linear density of the shortest path instead of the direct path is to handle the case where the distance between two sequential points in a periodic series is relatively large, e.g., the series (1, −1, . . . , 1, −1) has such a property. The STDE measurement of the periodicity has a few important characteristics: (a) the length of the periodic series does not affect its result; (b) the noise in the signal can decrease the quality of periodicity; (c) the measurement ranges from zero to infinity. FIG. 15 illustrates the quality of periodicity based on the STDE method for the signals of FIGS. 14A-14F (i.e., 1—sinusoid, 2—sinusoid with noise, 3—sawtooth, 4—synthetic sinusoid, 5—complicated synthetic sinusoid, and 6—random signal, respectively). It can be seen that:

1. the sinusoid and sawtooth have a quality larger than 40, and the random signal has a quality near zero;
2. the quality of sinusoid with light noise is half of the normal sinusoid;
3. the quality of double frequency sinusoid is lower than the normal sinusoid;
4. the complex sinusoid containing multiple frequency components has a very low quality even it is still periodical, because it takes a larger effort to repeat.

Accordingly, the STDE method described above can be used to calculate a quality of periodicity of a signal. This disclosure contemplates that the signal is not limited to the motion series described in the examples herein. It should be understood that the STDE method can optionally be implemented using a computing device (e.g., the computing device 200 of FIG. 2).

The method can include receiving a signal, transforming the signal into a spatial domain, identifying an attractor formed by the signal in the spatial domain, and calculating a quantitative measure of the periodicity of the signal based on the attractor. Optionally, the signal can be transformed into a spatial domain using Time-Delay Embedding (TDE). Additionally and optionally, the method can further include determining a linear length between at least two points of the attractor. Additionally, the method can optionally further include identifying a shortest linear length between at least two points of the attractor. The quantitative measure of the periodicity of the signal can be calculated as a linear density of a shortest linear length between at least two points of the attractor.

In some implementations, the STDE method described above can be used to calculate a quantitative measure of the subject's limb motion such as a quality of periodicity of limb trajectory. The STDE method can be applied to a motion series. It should be understood that the STDE method can optionally be implemented using a computing device (e.g., the computing device 200 of FIG. 2). The method can include extracting a motion series from the image data, and transforming the motion series into a spatial domain. As described above, the motion series can be extracted from the image data captured by a thermal camera (e.g., the thermal imaging device 104 of FIGS. 1A and 1B). In addition, the motion series can be transformed into a spatial domain using Time-Delay Embedding (TDE). The quantitative measure of the subject's limb motion can be calculated by deriving a quality of periodicity of limb trajectory based on the motion series in the spatial domain. For example, the quality of periodicity of limb trajectory can be derived by calculating a linear density of a shortest path of an attractor formed by the motion series in the spatial domain. Optionally, the subject's limb motion can optionally be a trajectory of at least a portion of the subject's foot. For example, the subject's limb motion can optionally be a trajectory of the subject's toe, the subject's heel, or the subject's foot angle.

Balance Capability of the Subject (Feet Balance Measurement)

Figure 16:
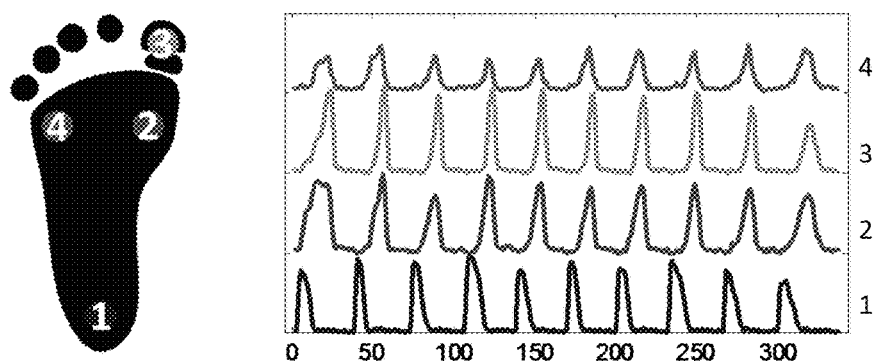
FIG. 16 illustrates four pressure sensors placed on the insole of a subject's foot to measure four areas of applied pressure.

The plantar pressure distribution in spatial and temporal domain contains rich information about human walking. The balancing capability of patients in their rehabilitation training is described in the examples below. Thus, only the spatial distribution of the plantar pressure is considered. It should be understood, however, that other pressure distributions may provide useful information. As described above, pressure sensors (e.g., the pressure sensors 102 of FIGS. 1A and 1B) can be used to detect plantar pressure. For example, FIG. 16 illustrates four pressure sensors placed on the insole of the subject's feet to measure four areas of the foot pressure. These areas cover the front, back, left and right side of the foot, and sustain a large plantar pressure load. Fourier Transform can be applied to the signal detected by each sensor to obtain its power spectrum, and the value of the highest peak in the power spectrum can be chosen as the pressure level. The pressure level of these four points form a rough plantar pressure distribution of one foot, and two feet generates eight pressure level points, which is denoted by a pressure vector p with eight elements as follows:

$$p=[p_{11},p_{12},p_{13},p_{14},p_{21},p_{22},p_{23},p_{24}], \quad (8)$$

This pressure vector is directly used as the feature vector to recognize different balance situations. In the 8-dimensional feature space, the pressure feature vector can indicate the following situations:

1. which leg of the patient is weak;
2. if the patient uses too much front/back foot;
3. if the patient uses too much outer/inner side of foot.

In other words, the pressure feature vector can be used for identifying a weak or disabled limb, an abnormal walking condition, or an imbalance of the subject. These cases actually reveal the conditions of leg muscles for the patient, and the physical therapist thus can give more useful advice on the next-step training based on the distribution of plantar pressure.

In some implementations, the quantitative measure of the subject's limb motion can optionally be calculated as a balance capability such as a plantar pressure distribution. It should be understood that plantar pressure distribution can optionally be calculated using a computing device (e.g., the computing device 200 of FIG. 2). For example, the method can optionally include determining a pressure distribution between the subject's feet. The quantitative measure of the subject's limb motion can be calculated by determining a balance capability of the subject based on the pressure distribution between the subject's feet.

EXAMPLES AND RESULTS

The example results are composed of three parts: motion recognition and segmentation, quality of periodicity, and feet balance measurement. The experiment platform was similar to the rehabilitation system described with regard to FIGS. 1A and 1B. For example, wireless pressure sensors (e.g., thin film pressure sensors) were incorporated into the insoles of the subject's footware, and the wireless module is tied outside. These sensors detected force or pressure of the subject's foot. A thermal camera is deployed right beside the treadmill. This sensor captured the thermal image data.

The presented PMTW is for 1-D time series data, but it can be generalized to high-dimensional data by matching the peak patterns respectively in each dimension. The skeleton of the lower limbs extracted from the thermal images has eight skeleton nodes in the 2-D plane, so there are 8×2=16 dimensions in total. As described above, one recommended measure of walking is the height of raising legs. In the example, the quality of walking was evaluated by checking the amplitude of raising legs in the walking cycles.

Figure 17:
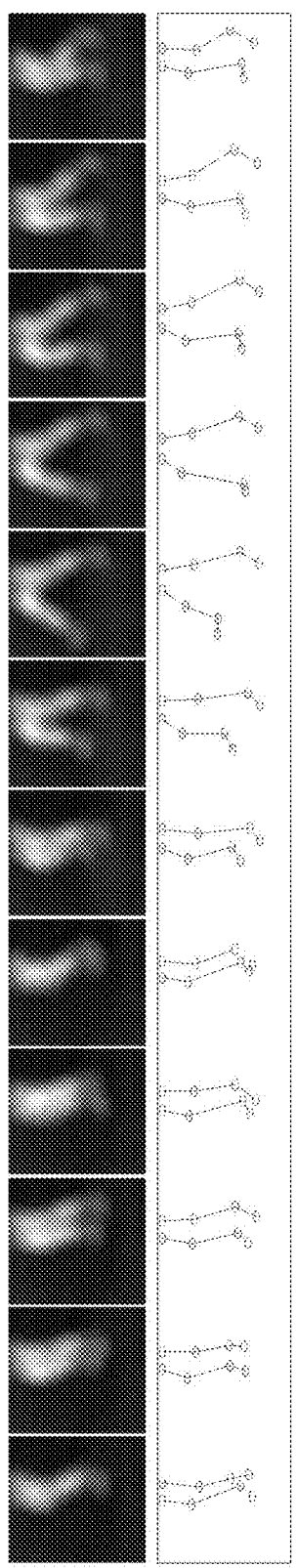
FIG. 17 illustrates the thermal images and extracted leg skeleton data showing the subject first walking with small stride, and then walking with higher legs.

The tested subject walks on the treadmill, and the user-interface displays suggestions on the screen if the subject needs higher stride. FIG. 17 illustrates the thermal images and extracted leg skeleton data showing that the subject first walks with small stride, and then starts to walk with higher legs. A simplified way to deal with high-dimensional data is to calculate the total distance of all skeletons to an origin skeleton. The skeleton origin is set to the posture of normal standing case, and an Euclidean distance is calculated between the skeleton origin and the skeleton data in each frame of the motion series.

Figure 18A:
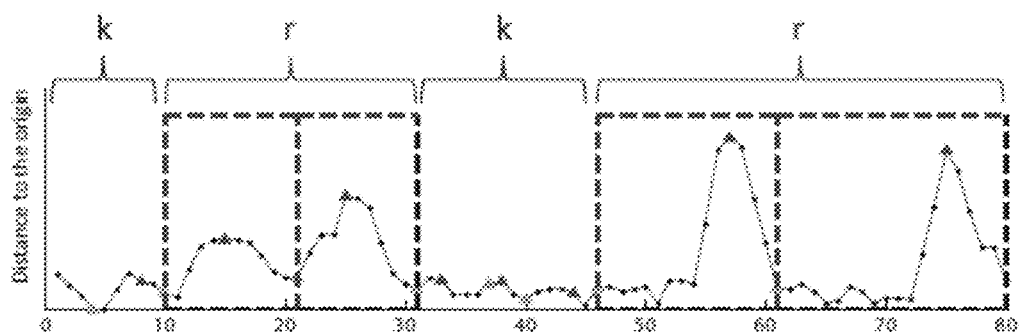
FIGS. 18A and 18B are example time series with its elements as the distance from the origin.
Figure 18B:
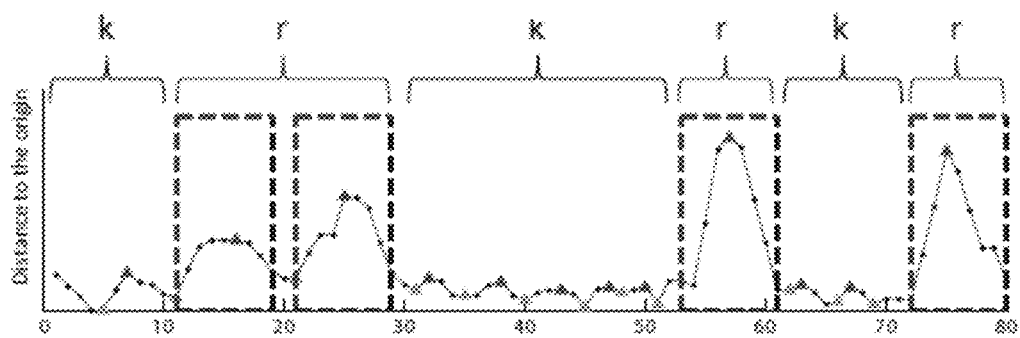

FIGS. 18A and 18B are example time series with its elements as the distance from the origin. The PMTW segmentation is applied to this distance time series to find the walking cycles. In this example, the motion series of the subject contains four sections: (1) two walking cycles with small steps; (2) two walking cycles with moderate high legs; (3) three walking cycles with small steps; (4) two walking cycles with very high legs.

The segmentation of the motion series by human observations of the thermal images (i.e., manual segmentation) is shown in FIG. 18A. The segmentation implemented by the PMTW described above is shown in FIG. 19B. It can be seen that the walking cycles with high legs have a much larger distance to the origin skeleton. In these figures, "r" denotes recognized and normal walking cycle, and "k" denotes recognized but abnormal walking cycle. All the walking cycles are recognized by the PMTW method, and the PMTW-based segmentation is almost the same as the manual segmentation, but the PMTW method can recognize more small walking cycles between the last two large cycles. Such details cannot be easily captured by medical personnel in conventional physical therapy.

Comparing to other segmentation methods, PMTW does not need to define many parameters such as the length of the segments, and it is also not sensitive to the noise or initial values. These properties make it work well for practical time series data.

The selection of template series is important for the PMTW-based segmentation. It may be possible to estimate the amplitudes of the tested series besides recognizing them. If the amplitude of the template is between the largest and smallest amplitude of the segments, it cannot distinguish if the segments have a larger and a smaller amplitude. This is because the distance between segments and the template does not consider the "+/−" signs. One way to solve this problem is to use a template with amplitudes larger than the largest one in the tested segment. And the distance between the template and the tested segment is normalized by the amplitude of the template, such that the threshold of recognition does not need to vary for different templates.

In the example, the positive half of the sinusoid with very large amplitude is used as the template. The PMTW method can find the segments that match with the positive half sinusoid. The distance between the segments and the template will be smaller if the matching segments have a larger amplitude. The generated segmentation result shows that the walking cycles with small steps are recognized but with a low score, and the walking cycles with higher legs are recognized with a high score. These results can guide the subjects to improve their gaits. For a more accurate evaluation, the templates prescribed by the therapist can be used.

Quality of Periodicity of Limb Motion

Figure 19:
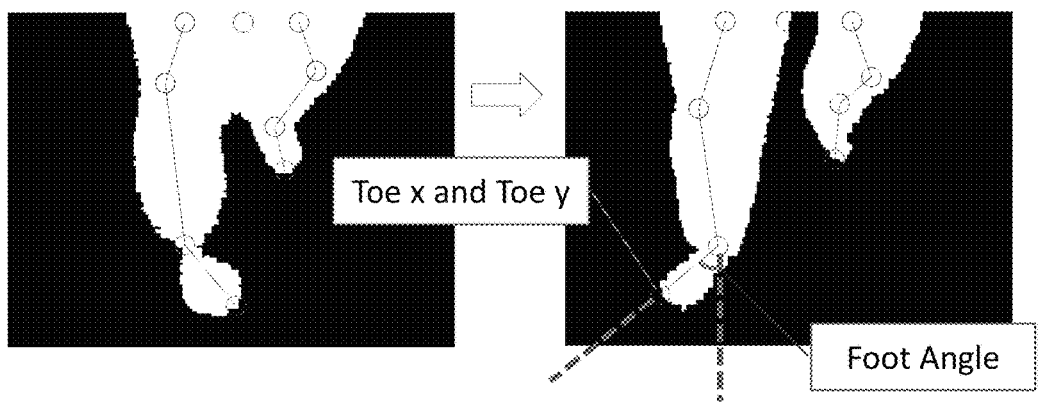
FIG. 19 illustrates the foot skeleton with two skeleton joints (toe and heel within the thermal images.
Figure 20:
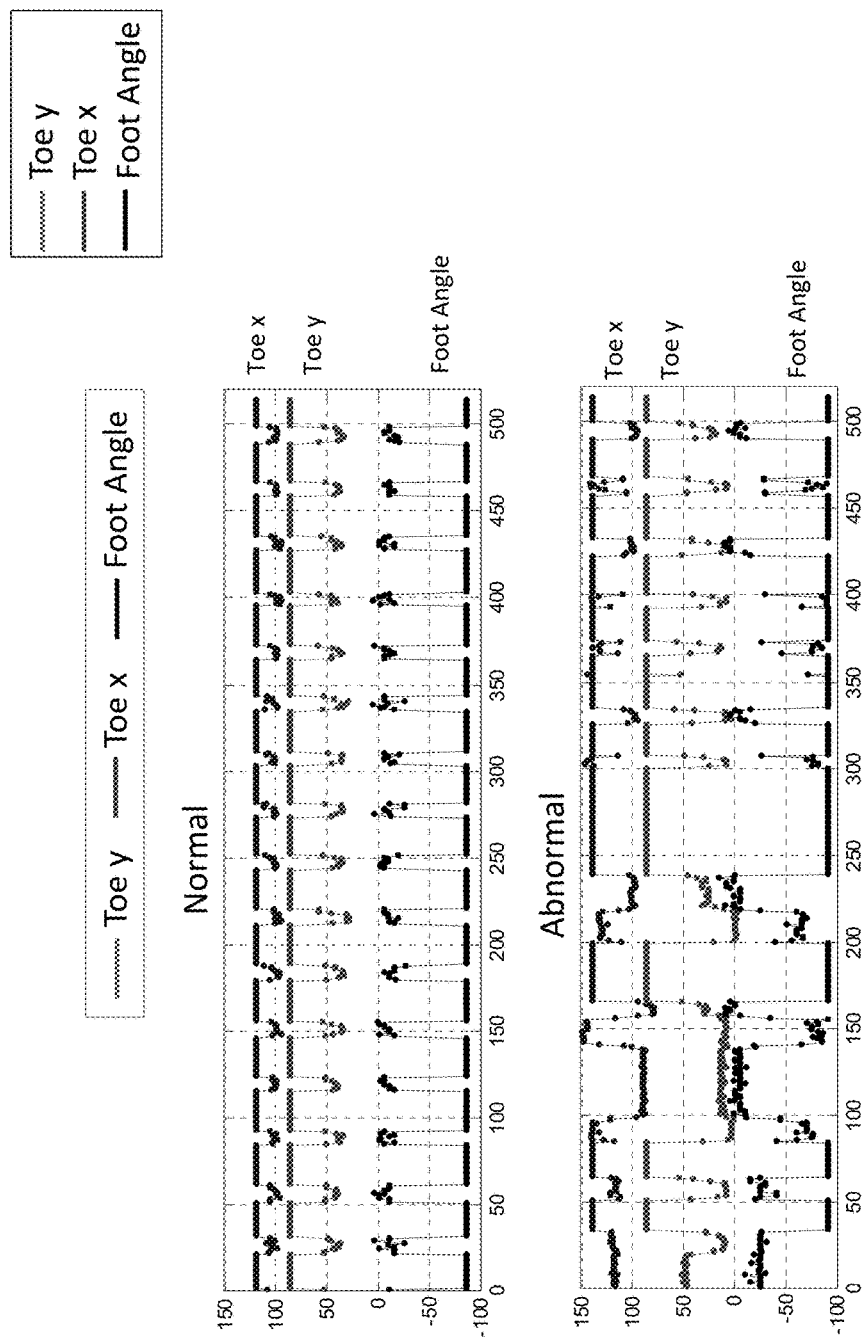
FIG. 20 illustrates a comparison between time series of the foot motion between normal walking and abnormal walking.
Figure 21:
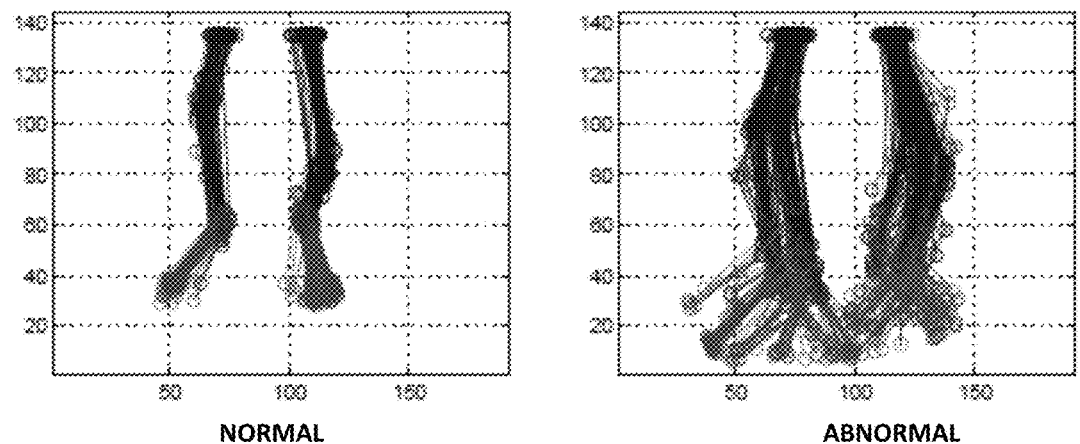
FIG. 21 illustrates a comparison of foot trajectory between normal and abnormal walking.

To evaluate the periodicity, the periodicity of the foot trajectory is the focus in the example. The foot trajectory is used instead of the whole lower-limb trajectory since the foot trajectory is effective to determine the quality of periodicity of the lower-limb motions. If the foot trajectory of the subject has a high repeatability, it typically means that the subject is making good progress. FIG. 19 illustrates the foot skeleton with two skeleton joints (toe and heel within the thermal images). These two joints have four coordinates in total (($x_1, y_1$) and ($x_2, y_2$)). The coordinates of the heel are not important if the coordinates of the toe are known. The variable that matters is the direction of the foot. Thus, the trajectory of $toe_x$, $toe_y$, and foot angle is traced, where $toe_x=x_1$, $toe_y=y_1$, and $footangle=\tan^{-1}((y_2-y_1)/(x_2-x_1))$. The quality of periodicity of the three variables will be considered separately. In most situations, once the foot strikes on the ground, it does not move anymore. Thus the area where the foot strikes is the focus. Besides, the supporting foot is usually blocked by the moving leg in the thermal image. Thus, the motion data after the foot has firmly struck on the ground is cut off, as shown in FIG. 20. Removing this part reduces the disturbance from the supporting foot and gives a more accurate quality of periodicity of the foot trajectory. FIG. 20 illustrates a comparison between time series of the foot motion between normal walking and abnormal walking. FIG. 21 illustrates a comparison of foot trajectory between normal and abnormal walking.

Figure 22:
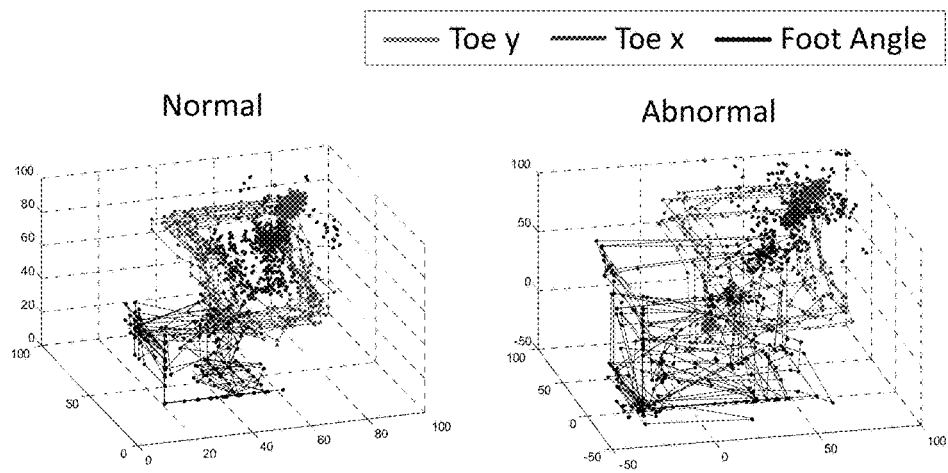
FIG. 22 illustrates a comparison of TDE results for normal and abnormal foot motion.
Figure 23:
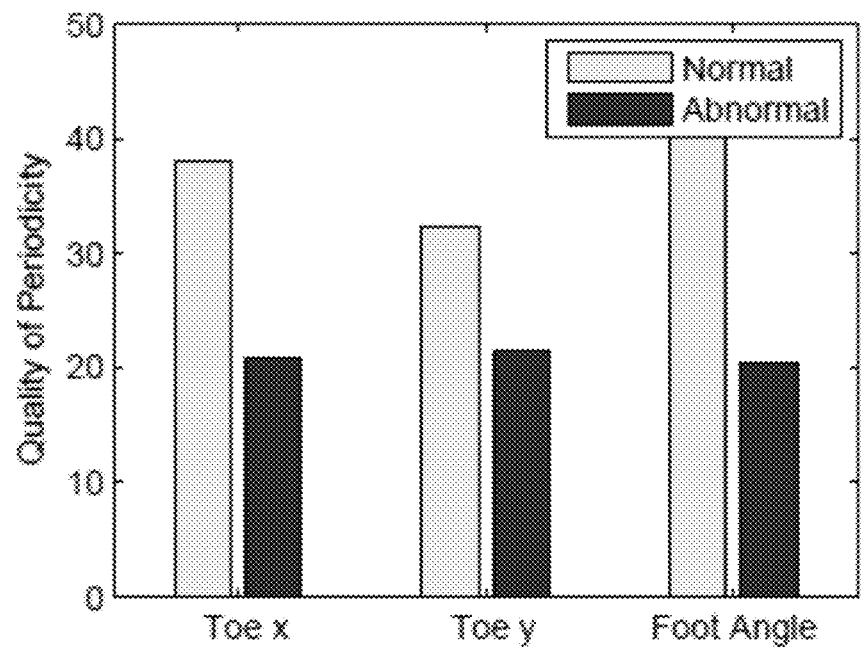
FIG. 23 illustrates the quantification result given by STDE for the quality of periodicity of foot trajectory for normal and abnormal walking.

The corresponding skeleton trajectories of the lower limbs are shown in FIG. 21. In FIG. 20, it can be seen that the abnormal walking style is more random in the temporal domain. In FIG. 21, it can be seen that the abnormal walking has a much larger striking area than the normal walking. Thus, it is possible to conclude that the abnormal walking is more random in the spatial domain. Intuitively, the striking area can be easily determined by the variance of the foot coordinates. But, in reality a periodic foot motion may cover a large striking area. Therefore both temporal and spatial domains should be considered to evaluate the quality of periodicity. By using STDE-based scheme, the spatial domain can be normalized and the periodicity can be quantified. Therefore, the time series shown in FIG. 20 are reconstructed by TDE method. FIG. 22 illustrates a comparison of TDE-based results for normal and abnormal foot motion. This shows that that the normal walking has more converged attractors for all the three time series. FIG. 22 illustrates that the attractors look like the attractor of sawtooth signal (i.e., FIG. 14C). FIG. 23 illustrates the quantification result given by STDE for the quality of periodicity of foot trajectory between normal and abnormal walking. Such a bar chart shows that the quality of periodicity of the abnormal waling is about half of the normal walking for all three variables.

Plantar Pressure Distribution

Figure 24:
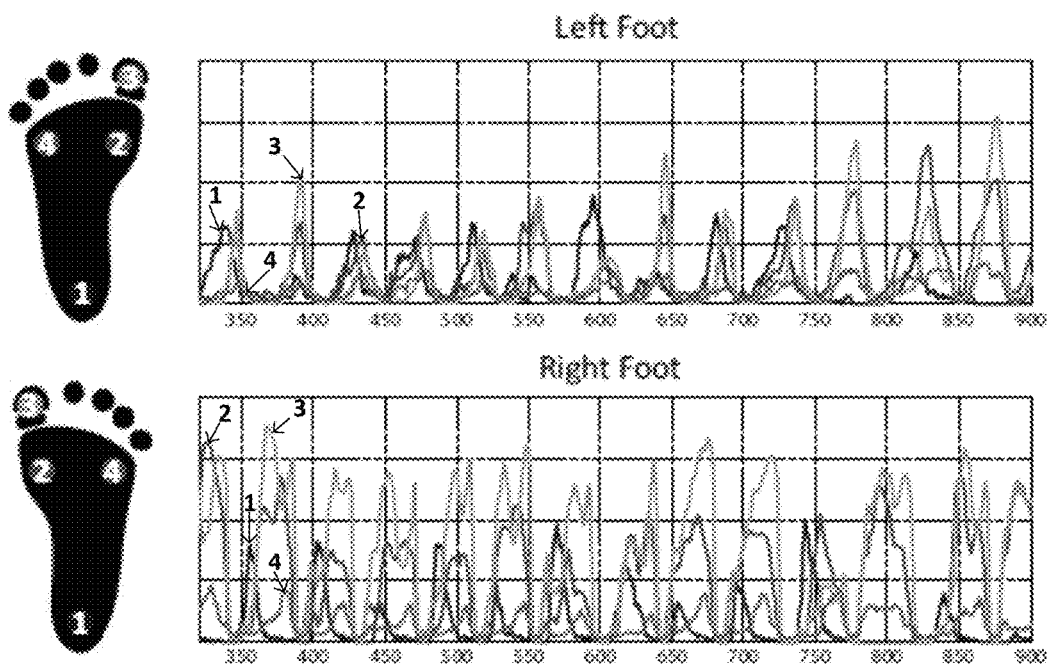
FIG. 24 illustrates the time series of the pressure signals for a subject with his left foot disabled.
Figure 25A:
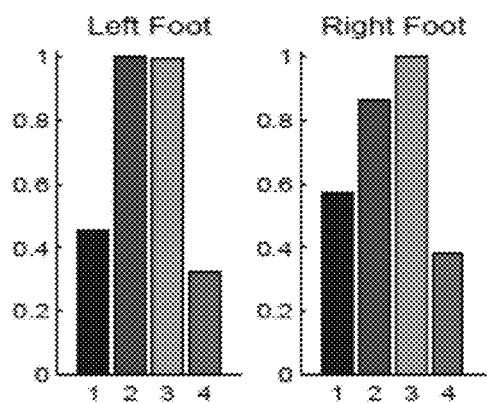
FIGS. 25A-25D illustrate the pressure distribution generated from the power spectrum for normal, right leg disabled, left leg disabled, and walking on outer foot edge cases, respectively.
Figure 25B:
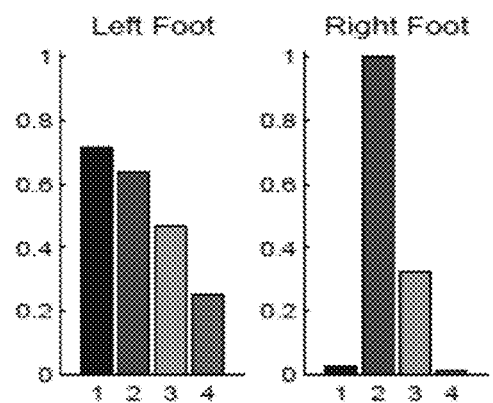
Figure 25C:
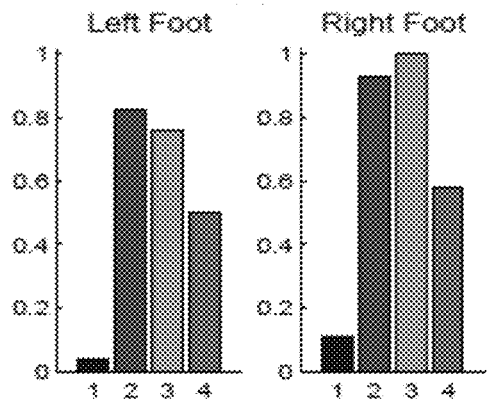
Figure 25D:
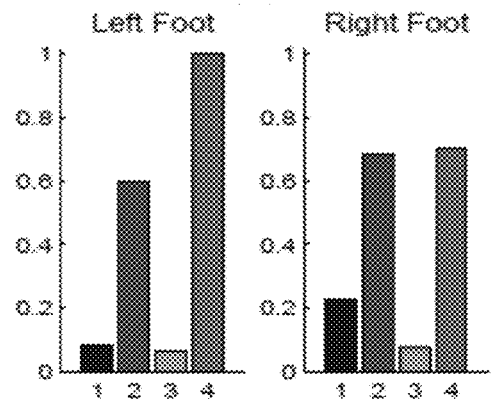

The sampling rate of the pressure sensor is 25 Hz. FIG. 24 illustrates the time series of the pressure signals for a subject with his left foot disabled. It can be seen that the pressure at the heel always comes first in each walking cycle. FIGS. 25A-25D illustrate the pressure distribution generated from the power spectrum for normal, right leg disabled, left leg disabled, and walking on outer foot edge cases, respectively. The pressure level is normalized by the maximum level within the eight pressure levels. The pressure distribution shows that:

1. the area near tiptoe sustains the largest pressure load in normal walking;

2. when one leg of the subject is disabled, the corresponding foot still sustains pressure, but the pressure is concentrated on a small area of the foot. In the example, it is concentrated on the front foot. The pressure distribution on the available foot is also influenced, because the imbalance between two feet has impact on the whole pressure distribution, not only on the disabled foot;

3. when the subject walks on his toes, the pressure at the heel is almost zero, and most of the pressure goes to the front foot;

4. when the subject walks on his outer edge of the feet, the pressure on the toe and the heel becomes pretty small, and the pressure is concentrated on the two sides of the foot.

By studying different walking cases, it is found that the area 3 on the foot is special: under all tests this area always supports the body unless one walks on his heel. Using the pressure feature vector in Eq. 8, the balancing capability of the subject can be classified via typical classification algorithms such as SVM. FIG. 26 illustrates the confusion matrix of the classification of foot balance. There is little misclassification between the disabled left leg walking and the normal walking 3, which may be because the subject 3 tends to use more of his left leg in the tests. For other situations, the classification performs well.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for rehabilitation of limb motion, comprising:
   at least one of a thermal imaging device for imaging a subject or a plurality of sensors for sensing force or pressure exerted by a portion of the subject's body;
   a processor; and
   a memory operably coupled to the processor, the memory having computer-executable instructions stored thereon that, when executed by the processor, cause the processor to:
   receive at least one of force or pressure data measured by the sensors or image data captured by the thermal imaging device, and
   calculate a quantitative measure of the subject's limb motion based on the force or pressure data or the image data.

2. The system of claim 1, wherein the sensors are configured to measure a respective pressure exerted by each of the subject's feet.

3. The system of claim 1, wherein the sensors are thin-film pressure sensors configured for placement in the subject's footwear.

4. The system of claim 1, wherein the thermal imaging device captures motion of the subject's lower limbs.

5. The system of claim 1, wherein the thermal imaging device is configured to transmit the image data over a wireless link, or wherein the sensors are configured to transmit the force or pressure data over a wireless link.

6. The system of claim 1, wherein the quantitative measure of the subject's limb motion comprises at least one of a height of raising a limb, a motion cycle similarity score, a quality of periodicity of limb trajectory, or a balance capability of the subject.

7. The system of claim 1, further comprising a display device, wherein the memory has further computer-executable instructions stored thereon that, when executed by the processor, cause the processor to generate an instruction related to the subject's limb motion based on the quantitative measure, and wherein the instruction is graphically displayed on the display device.

8. The system of claim 1, wherein the memory has further computer-executable instructions stored thereon that, when executed by the processor, cause the processor to:
   extract a motion series from the image data, the motion series defining the subject's limb motion in at least one dimension; and recognize one or more normal motion cycles within the motion series based on a comparison between a peak pattern of the motion series and a peak pattern of a template motion series, wherein the template motion series defines a normal motion cycle.

9. The system of claim 8, wherein the memory has further computer-executable instructions stored thereon that, when executed by the processor, cause the processor to recognize one or more abnormal motion cycles within the motion series based on the comparison between the peak pattern of the motion series and the peak pattern of the template motion series.

10. The system of claim 8, wherein calculating a quantitative measure of the subject's limb motion further comprises calculating a motion cycle similarity score between one or more peaks within the motion series and one or more peaks within the template motion series.

11. The system of claim 8, wherein the peak pattern comprises at least one of an amplitude, order, or speed of peaks.

12. The system of claim 1, wherein the memory has further computer-executable instructions stored thereon that, when executed by the processor, cause the processor to:
extract a motion series from the image data, the motion series defining the subject's limb motion in at least one dimension; and
transform the motion series into a spatial domain, wherein calculating a quantitative measure of the subject's limb motion further comprises deriving a quality of periodicity of limb trajectory based on the motion series in the spatial domain.

13. The system of claim 12, wherein transforming the motion series into a spatial domain comprises Time-Delay Embedding (TDE).

14. The system of claim 12, wherein deriving a quality of periodicity of limb trajectory based on the motion series in the spatial domain further comprises calculating a linear density of a shortest path of an attractor formed by the motion series in the spatial domain.

15. The system of claim 12, wherein the subject's limb motion comprises a trajectory of at least a portion of the subject's foot.

16. The system of claim 1, wherein the memory has further computer-executable instructions stored thereon that, when executed by the processor, cause the processor to determine a pressure distribution between the subject's feet, and wherein calculating a quantitative measure of the subject's limb motion further comprises determining a balance capability of the subject based on the pressure distribution between the subject's feet.

17. The system of claim 16, wherein the pressure distribution between the subject's feet is a plantar pressure distribution.

18. The system of claim 16, wherein the memory has further computer-executable instructions stored thereon that, when executed by the processor, cause the processor to identify at least one of a weak or disabled limb, an abnormal walking condition, or an imbalance of the subject.

* * * * *